(12) United States Patent
Kang et al.

(10) Patent No.: US 8,512,877 B2
(45) Date of Patent: Aug. 20, 2013

(54) NAPHTHYL CARBAZOLE DERIVATIVES, KL HOST MATERIAL, THE ORGANIC LIGHT EMITTING DEVICE EMPLOYING THE SAME, THE DISPLAY DEVICE AND THE ILLUMINATION DEVICE EMPLOYING THE SAME

(75) Inventors: Kyong Min Kang, Pyeongtaek-si (KR); Deug Sang Lee, Pyeongtaek-si (KR); Chang Jun Lee, Bucheon-si (KR); Kyoung Moon Go, Pyeongtaek-si (KR); Jong Soon Lee, Gwangmyeong-si (KR); Se Hoon Kim, Pyeongtaek-si (KR)

(73) Assignee: Dongwoo Fine-Chem, Seoul (KR)

( * ) Notice: Subject to any disclaimer, the term of this patent is extended or adjusted under 35 U.S.C. 154(b) by 622 days.

(21) Appl. No.: 12/593,869

(22) PCT Filed: Mar. 27, 2008

(86) PCT No.: PCT/KR2008/001716
§ 371 (c)(1),
(2), (4) Date: Oct. 22, 2009

(87) PCT Pub. No.: WO2008/120899
PCT Pub. Date: Oct. 9, 2008

(65) Prior Publication Data
US 2010/0156283 A1  Jun. 24, 2010

(30) Foreign Application Priority Data

Mar. 29, 2007 (KR) .................. 10-2007-0031148
Mar. 30, 2007 (KR) .................. 10-2007-0031821
Dec. 28, 2007 (KR) .................. 10-2007-0140745

(51) Int. Cl.
*H01L 51/54* (2006.01)

(52) U.S. Cl.
USPC ........ 428/690; 428/917; 257/40; 257/E51.05; 257/E51.026; 257/E51.032; 313/504; 313/505; 313/506; 548/440; 546/18; 546/24

(58) Field of Classification Search
USPC ...... 428/690, 917; 257/40, E51.05, E51.026, 257/E51.032; 313/504, 505, 506; 548/440; 546/18, 24
See application file for complete search history.

(56) References Cited

U.S. PATENT DOCUMENTS

2006/0088728 A1   4/2006 Kwong et al.
2007/0247063 A1*  10/2007 Murase et al. ............... 313/504

FOREIGN PATENT DOCUMENTS

| JP | 2005-213188 | * | 8/2005 |
| JP | 2005213188 | | 8/2005 |
| JP | 2007-063501 | | 3/2007 |
| JP | 2010-500830 | | 6/2012 |
| WO | 2005/113531 A1 | | 12/2005 |

OTHER PUBLICATIONS

Gong, Red Electrophosphorescence from a Soluble Binaphthol Derivative as Host and Iridium Complex as Guest, The Journal of Physical Chemistry B, 2006, 110 (14), pp. 7344-7348, University of California, Santa Barbara, CA, Published on Web.

* cited by examiner

*Primary Examiner* — Jennifer Chriss
*Assistant Examiner* — Gregory Clark
(74) *Attorney, Agent, or Firm* — Workman Nydegger

(57) ABSTRACT

Naphthylcarbazole derivatives are provided. The naphthylcarbazole derivatives are represented by Formula 1. Further provided are KL host materials, organic electroluminescent devices employing the host materials, and displays and lighting systems comprising the devices.

17 Claims, 16 Drawing Sheets
(14 of 16 Drawing Sheet(s) Filed in Color)

NAPHTHYL CARBAZOLE DERIVATIVES, KL HOST MATERIAL, THE ORGANIC LIGHT EMITTING DEVICE EMPLOYING THE SAME, THE DISPLAY DEVICE AND THE ILLUMINATION DEVICE EMPLOYING THE SAME

TECHNICAL FIELD

The present invention relates to naphthylcarbazole derivatives, KL host materials, organic electroluminescent devices employing the host materials, and displays and lighting systems comprising the devices. More particularly, the present invention relates to organic electroluminescent devices that have a simple structure, exhibit high luminescence efficiency and can maintain their chromaticity coordinates constant irrespective of variations in operating voltage and/or current density.

BACKGROUND ART

Organic electroluminescent devices are self-luminous devices based on the phenomenon that electrons combine with holes in a fluorescent or phosphorescent organic layer when a current is applied to the organic layer to generate light. Such organic electroluminescent devices have the advantages of light weight, a small number of components and relatively simple fabrication processes.

Particularly, white organic electroluminescent devices can find applications as light sources for a variety of electric devices, such as liquid crystal displays, and backlight units. White organic electroluminescent devices can also be combined with other elements, such as color filters, in the manufacture of full-color displays.

However, conventional white organic electroluminescent devices have failed to provide satisfactory results in terms of electrical properties, including luminance, current density, power efficiency and chromaticity coordinates.

FIG. 1 is a diagram illustrating the mechanism of light emission from a conventional organic electroluminescent device. As illustrated in FIG. 1, holes are injected into the valance band or the highest-occupied molecular orbital (HOMO) of a material for a hole injection layer (HIL) and enter a light-emitting layer through a hole-transporting layer (HTL), and at the same time, electrons migrate from a cathode to the light-emitting layer through an electron injection layer. The holes combine with the electrons in the light-emitting layer to form excitons, after which the excitons fall to the ground state to emit light.

In the energy transfer process, singlet excitons and triplet excitons are involved in fluorescence and phosphorescence emission, respectively. Therefore, fluorescence can contribute to a maximum of 25% and phosphorescence can contribute to a maximum of 75% in energy efficiency. However, it is known that either singlet or triplet excitons can emit light and both singlet and triplet excitons cannot participate in energy transfer.

An organic electroluminescent device with improved energy efficiency was reported wherein a plurality of light-emitting layers contain the same host and are divided into individual layers emitting fluorescence or phosphorescence (*Nature* vol. 440, 908 (13, Apr. 2006)).

The structure of the conventional device is shown in FIG. 2. Specifically, the device comprises an anode 110, which is made of indium tin oxide (ITO) by vacuum deposition, a hole injection layer 120, a hole-transporting layer 130, a multi-layer structure of a fluorescent layer 140, a green phosphorescent layer 150 and a red phosphorescent layer 160 as light-emitting layers, each of which emits monochromatic light, a hole-blocking layer 170, an electron-transporting layer 180, an electron injection layer 190 and a cathode 200 formed in this order on a transparent substrate 100 by vacuum deposition wherein different colors of light from the light-emitting layers are mixed together to emit polychromatic light.

The organic electroluminescent device is configured to emit fluorescence and phosphorescence from the multilayer structure of light-emitting layers rather than from a single light-emitting layer. In the organic electroluminescent device, electrons are injected from the cathode 200 to the light-emitting layers 140, 150 and 160 through the electron-transporting layer 180, and holes are injected from the anode 110 to the light-emitting layers 140, 150 and 160 through the hole-transporting layer 130. The electrons combine with the holes in the light-emitting layers to form electron-hole pairs (i.e. excitons). The excitons recombine in the respective light-emitting layers containing the same host to allow a fluorescent dopant of the fluorescent layer 140 to emit blue light, a green phosphorescent dopant of the green phosphorescent layer 150 to emit green light and a red phosphorescent dopant of the red phosphorescent layer 160 to emit red light. The different colors of light from the light-emitting layers 140, 150 and 160 are mixed to emit white light. However, the presence of the three light-emitting layers renders the structure of the organic electroluminescent device complex.

Further, an attempt has been made to achieve white light emission using complementary colors (SID 2006, NOV-ALED). This attempt, however, has many limitations in that the limited complementary color relationship causes poor luminescence efficiency and insufficient intensity of light in a particular wavelength region results in poor color reproducibility.

Thus, there is a need to develop organic electroluminescent devices that have a simple structure, exhibit high luminescence efficiency and have high color reproducibility. There is also a need to develop white organic electroluminescent devices that can maintain their chromaticity coordinates constant irrespective of variations in operating voltage and/or current density.

DISCLOSURE

Technical Problem

The present invention has been made in an effort to solve the above problems, and it is one object of the present invention to provide a host material capable of simultaneously emitting fluorescence and phosphorescence in a single layer while exhibiting high luminescence efficiency.

It is another object of the present invention to provide a novel naphthylcarbazole derivative suitable for use as a host material that is capable of simultaneously emitting fluorescence and phosphorescence in a single layer while exhibiting high luminescence efficiency.

It is another object of the present invention to provide an organic electroluminescent device that has a simple structure and exhibit high luminescence efficiency.

It is still another object of the present invention to provide a display and a lighting system that have a high luminescence efficiency, a wide color reproduction range and a high color purity.

Technical Solution

In accordance with one aspect of the present invention, there is provided a naphthylcarbazole derivative of Formula 1:

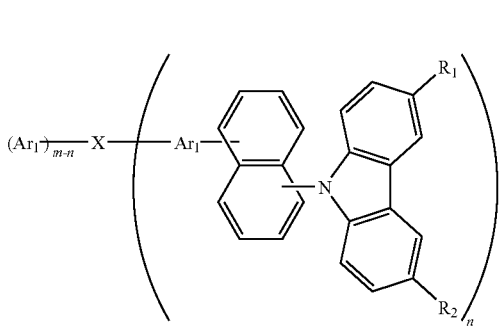

(1)

wherein each $Ar_1$ is selected from the group consisting of substituted or unsubstituted $C_6$-$C_{30}$ aromatic hydrocarbon groups which optionally contain at least one unsaturated aliphatic moiety, $C_2$-$C_{10}$ unsaturated aliphatic hydrocarbon groups, and substituted or unsubstituted $C_2$-$C_{24}$ unsaturated heterocyclic groups; $R_1$ and $R_2$ are each independently selected from the group consisting of hydrogen, $C_6$-$C_{24}$ aromatic hydrocarbon groups, and $C_6$-$C_{30}$ aromatic hydrocarbon groups containing at least one unsaturated aliphatic moiety; and X is selected from the group consisting of carbon, silicon, oxygen and sulfur, provided that when X is carbon or silicon, m is 4 and n is an integer from 1 to 4 and that when X is oxygen or sulfur, m is 2 and n is 1 or 2.

In a preferred embodiment, each $Ar_1$ is selected from the following structures 2-1:

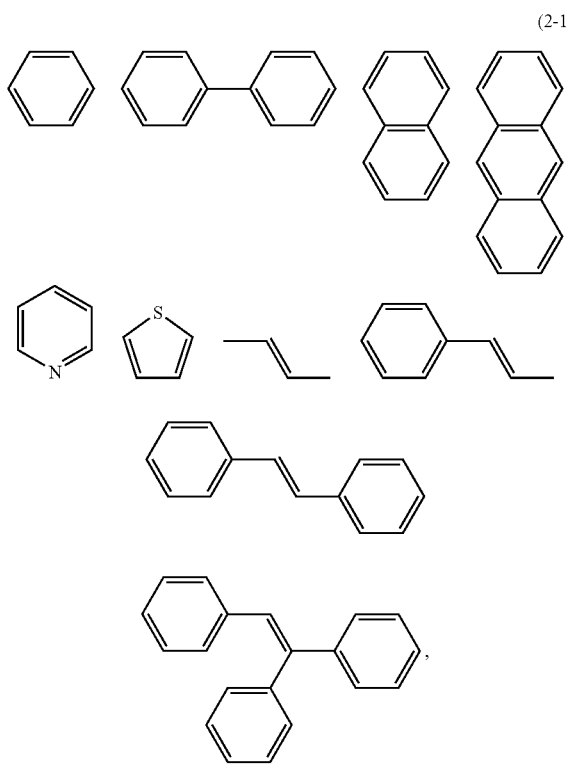

(2-1)

and $R_1$ and $R_2$ are each independently selected from the following structures 2-2:

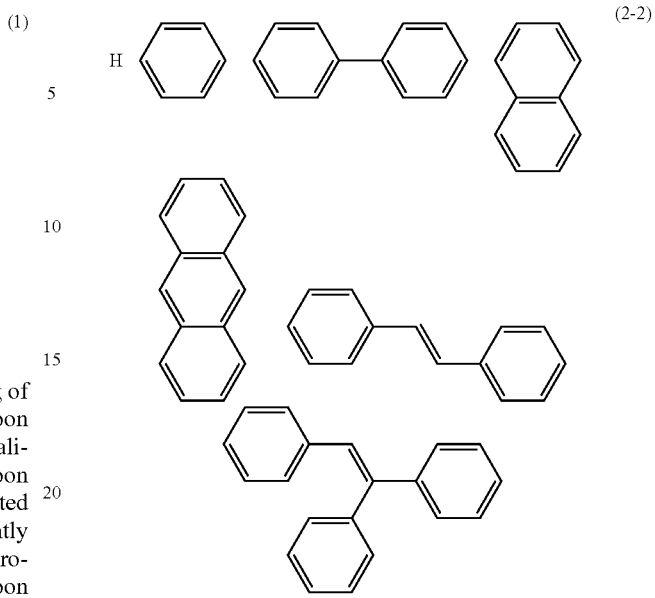

(2-2)

In accordance with another aspect of the present invention, there is provided a KL host material for the formation of a light-emitting layer of an organic electroluminescent device wherein when the host material is combined with at least one dopant of fluorescent and phosphorescent dopants to form the light-emitting layer, energy of the host material is transferred to at least one dopant of the fluorescent and phosphorescent dopants to allow the dopant to emit light, and at the same time, the host material emits light of its own.

In an embodiment of the present invention, the KL host material may be the carbazole derivative of Formula 1.

In accordance with another aspect of the present invention, there is provided an organic electroluminescent device comprising an anode, a cathode and at least one light-emitting layer between the anode and the cathode wherein the light-emitting layer contains the KL host material.

In an embodiment of the present invention, the light-emitting layer may further contain at least one dopant of phosphorescent and fluorescent dopants.

In an embodiment of the present invention, the KL host material may emit light and the dopant may emit light in a single layer.

In an embodiment of the present invention, the light-emitting layer may simultaneously emit fluorescence and phosphorescence.

In an embodiment of the present invention, the light-emitting layer may have a multilayer structure of two or more layers containing the KL host material and different dopants.

In an embodiment of the present invention, the light-emitting layer or the multilayer structure of two or more layers may have a thickness of 1 to 60 nm and preferably 10 to 60 nm.

In an embodiment of the present invention, when the light-emitting layer has a multilayer structure of two or more layers, the KL host materials of the multilayer structure may be identical to or different from each other.

In an embodiment of the present invention, when the light-emitting layer has a multilayer structure of two or more layers, the dopants may be different phosphorescent dopants, a phosphorescent dopant and a fluorescent dopant, or different fluorescent dopants. Preferably, the dopants are different phosphorescent dopants.

In an embodiment of the present invention, the dopant may be present in an amount of 0.5 to 35 parts by weight, based on 100 parts by weight of the light-emitting layer.

In an embodiment of the present invention, light from the KL host material may be mixed with light emitted from the dopant due to the energy transfer of the KL host material.

In an embodiment of the present invention, the mixed light may be white light.

In an embodiment of the present invention, the KL host material may emit blue light.

In an embodiment of the present invention, no hole-blocking layer may be formed between the cathode and the light-emitting layer.

In accordance with yet another aspect of the present invention, there are provided a display and a lighting system comprising the organic electroluminescent device.

DESCRIPTION OF DRAWINGS

The patent or application file contains at least one drawing executed in color. Copies of this patent or patent application publication with color drawing(s) will be provided by the Office upon request and payment of the necessary fee.

In the figures.

Best Mode

The present invention will now be described in greater detail. However, the following description serves to provide further appreciation of the invention but is not meant in any way to restrict the scope of the invention.

First, an explanation of the term 'KL host' used herein will be provided below.

Figure 1:
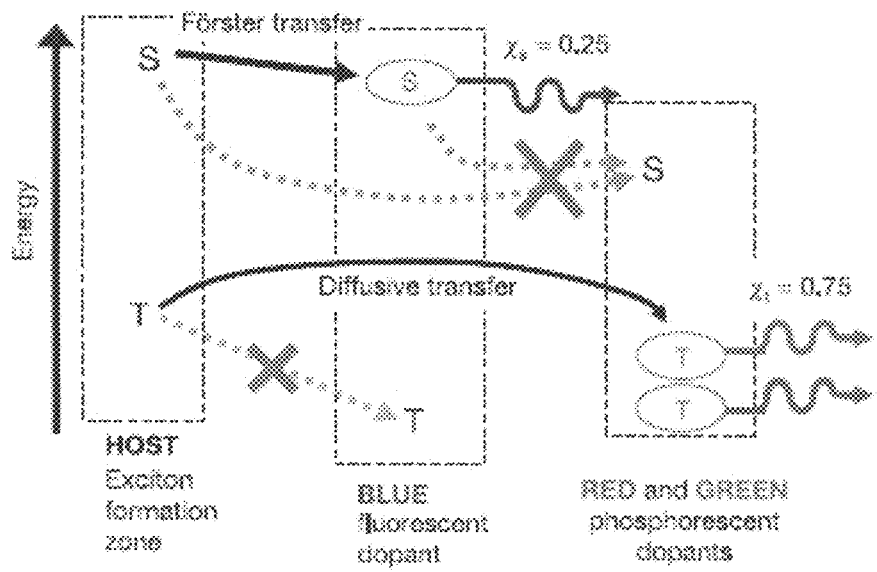
FIG. 1 is a model diagram illustrating the mechanism of light emission from a conventional organic electroluminescent device.
Figure 2:
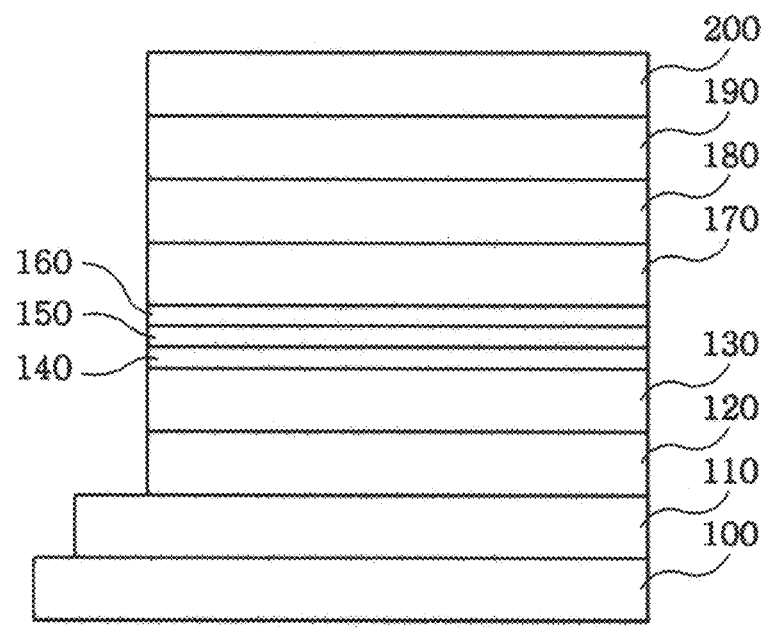
FIG. 2 is a view of a conventional organic electroluminescent device having a multilayer structure of a plurality of light-emitting layers.
Figure 3:
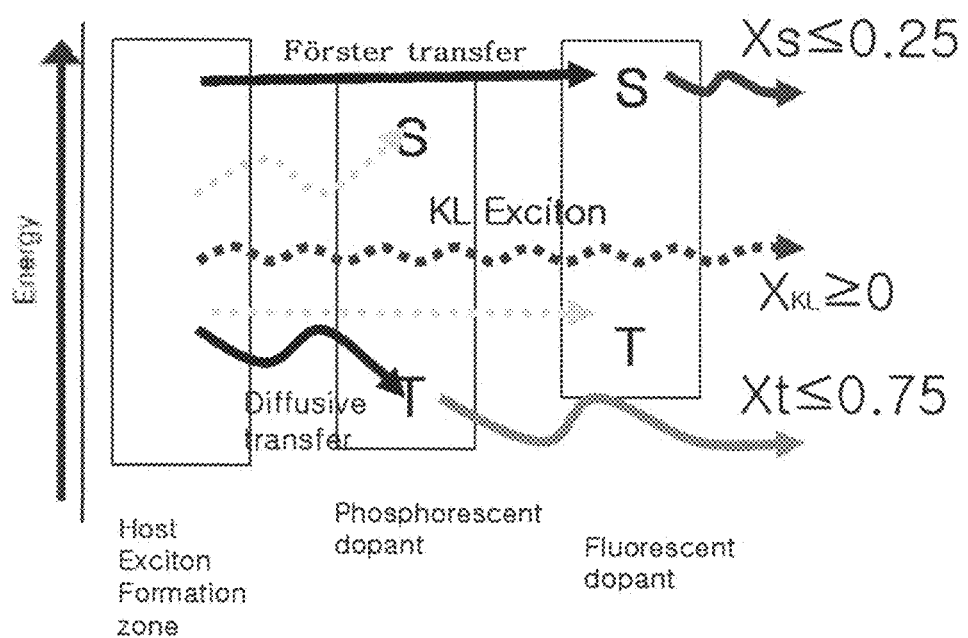
FIG. 3 is a model diagram illustrating the mechanism of light emission from an organic electroluminescent device of the present invention.

The 'KL host' is a new concept introduced and defined by the present inventors. When a luminescent host material is combined with a dopant in a conventional organic electroluminescent device, no light is emitted from the luminescent host material, and instead, energy of the luminescent host material is transferred to the dopant to allow the dopant to emit light, such as fluorescence or phosphorescence. In contrast, as illustrated in the mechanism of FIG. 3, when the newly defined 'KL host' is combined with fluorescent and phosphorescent dopants, energy of the KL host material is transferred to at least one dopant of the fluorescent and phosphorescent dopants to simultaneously allow the KL host material as well as the dopant to emit light. The 'KL host' features this simultaneous emission of light (herein, excitons contributing to the emission of light from the KL host material are termed 'KL excitons').

The present inventors have succeeded in developing very useful compounds as KL host materials. The compounds have the following advantages. Firstly, doping of one of the KL host materials with a phosphorescent dopant simultaneously allows the host material to emit fluorescence and the dopant to emit phosphorescence. This simultaneous light emission can achieve the maximum fluorescence efficiency (25%) and the maximum phosphorescence efficiency (75%) to reach the theoretical maximum efficiency (100%). That is, the maximum efficiency can be attained in a simple manner, such as doping. The greatest advantage associated with the use of the KL host material is that a single light-emitting layer can be used to simplify the structure of a device. Secondly, the KL host material can be combined with a phosphorescent dopant and/or a fluorescent dopant to form a single light-emitting layer of a device. This combination allows for mixing of light from the KL host material with phosphorescence from the phosphorescent dopant and/or fluorescence from the fluorescent dopant to emit polychromatic light (e.g., white light), resulting in increased luminescence efficiency of the device.

A compound particularly useful as the KL host material has a structure of Formula 1:

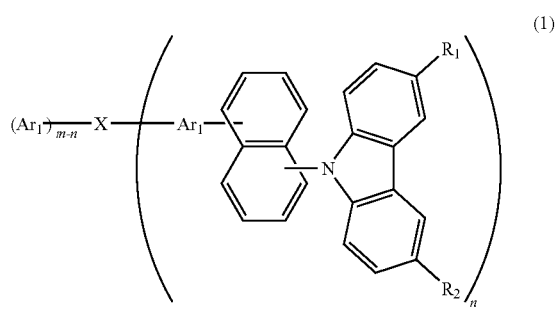

wherein each $Ar_1$ is selected from the group consisting of substituted or unsubstituted $C_6$-$C_{30}$ aromatic hydrocarbon groups which optionally contain at least one unsaturated aliphatic moiety, $C_2$-$C_{10}$ unsaturated aliphatic hydrocarbon groups, and substituted or unsubstituted $C_2$-$C_{24}$ unsaturated heterocyclic groups; $R_1$ and $R_2$ are each independently selected from the group consisting of hydrogen, $C_6$-$C_{24}$ aromatic hydrocarbon groups, and $C_6$-$C_{30}$ aromatic hydrocarbon groups containing at least one unsaturated aliphatic moiety; and X is selected from the group consisting of carbon, silicon, oxygen and sulfur, provided that when X is carbon or silicon, m is 4 and n is an integer from 1 to 4 and that when X is oxygen or sulfur, m is 2 and n is 1 or 2.

The term "aromatic hydrocarbon group" refers to a $C_6$-$C_{30}$ mono- or polycyclic moiety, for example, phenyl, biphenyl, anthracenyl or naphthyl.

The term "unsaturated aliphatic hydrocarbon group" refers to a hydrocarbon group containing one or more double or triple bonds in the molecule, for example, buten-2-yl, penten-2-yl or pentyn-2-yl.

The term "heterocyclic group" refers to a saturated or unsaturated cyclic group containing at least one heteroatom selected from O, N and/or S, preferably N and/or S, and 1 to 24 carbon atoms. Examples of such heterocyclic groups include pyrrolidyl, tetrahydrofuranyl, dihydrofuranyl, tetrahydrothienyl, tetrahydropyranyl, dihydropyranyl and dihydrothienyl.

The term "substituted or unsubstituted" describes that the above functional groups, e.g., "aromatic hydrocarbon groups", "unsaturated aliphatic hydrocarbon groups" and "heterocyclic groups", may be optionally substituted with one to five substituents selected from the group consisting of $C_1$-$C_6$ alkyl, $C_1$-$C_6$ alkylaryl, $C_1$-$C_6$ alkylheteroaryl, $C_2$-$C_6$ alkenyl, $C_2$-$C_6$ alkynyl, primary, secondary and tertiary amino groups, quaternary ammonium moieties, acyl, acyloxy, acylamino, aminocarbonyl, alkoxycarbonylamino, alkoxycarbonyl, aryl, aryloxy, heteroaryl, heteroaryloxy, carboxyl, cyano, halo, hydroxyl, nitro, sulfanyl, sulfoxy, sulfonyl, sulfonamido, alkoxy, thioalkoxy and trihalomethyl, without being bound by the definitions of the respective substituents.

When n is 1 and $Ar_1$ and carbazole are attached to the 1- and 4-positions of the naphthalene ring in Formula 1, the compound has a structure of Formula 1-1:

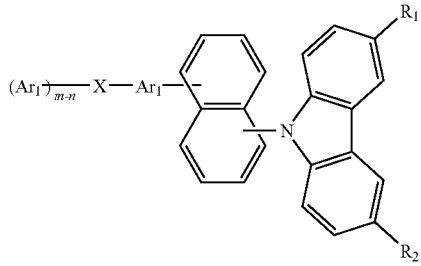

(1-1)

wherein $Ar_1$, $R_1$, $R_2$ and X are as defined in Formula 1, provided that when X is carbon or silicon, m-n is 3 and that when X is oxygen or sulfur, m-n is 1.

When n is 2 and $Ar_1$ and carbazole are attached to the 1- and 4-positions of the naphthalene ring in Formula 1, the compound has a structure of Formula 1-2:

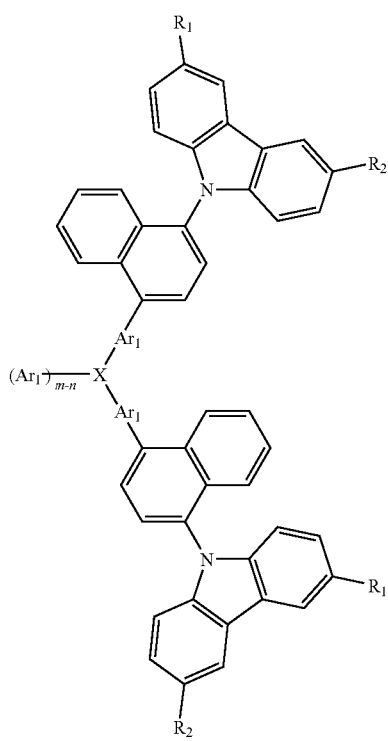

(1-2)

wherein $Ar_1$, $R_1$, $R_2$ and X are as defined in Formula 1, provided that when X is carbon or silicon, m-n is 2 and that when X is oxygen or sulfur, m-n is nothing (i.e. zero).

When n is 4 and $Ar_1$ and carbazole are attached to the 1- and 4-positions of the naphthalene ring in Formula 1, the compound has a structure of Formula 1-3:

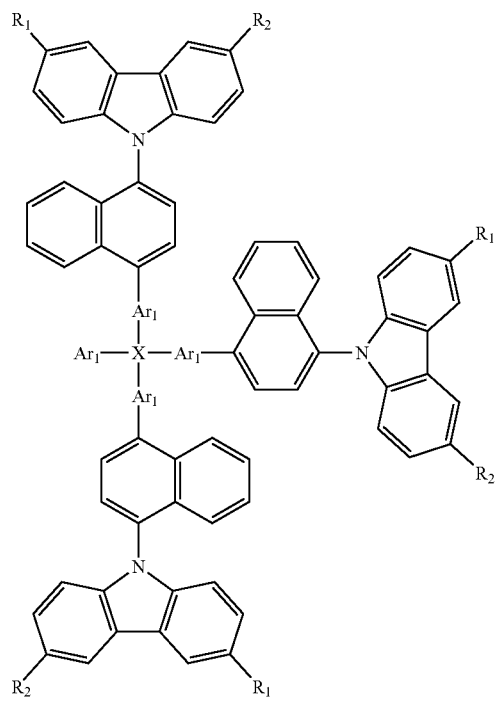

(1-3)

wherein $Ar_1$, $R_1$ and $R_2$ are as defined in Formula 1 and X is carbon or silicon.

When n is 4 and $Ar_1$ and carbazole are attached to the 1- and 4-positions of the naphthalene ring in Formula 1, the compound has a structure of Formula 1-4:

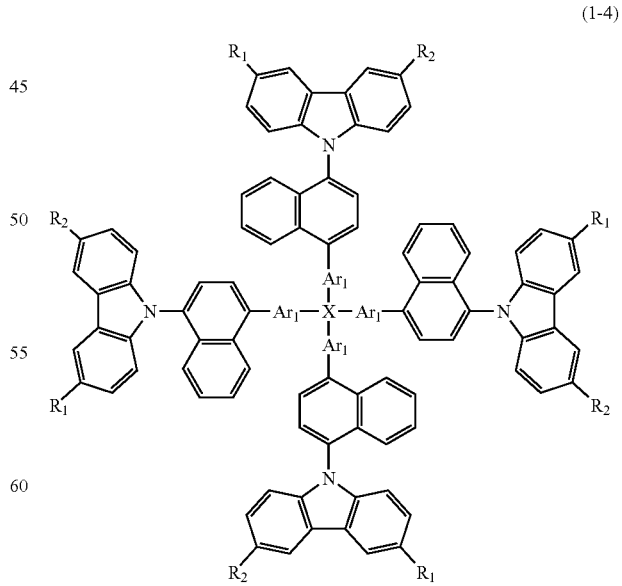

(1-4)

wherein $Ar_1$, $R_1$ and $R_2$ are as defined in Formula 1 and X is carbon or silicon.

In Formula 1, each $Ar_1$ is selected from the following structures 2-1:

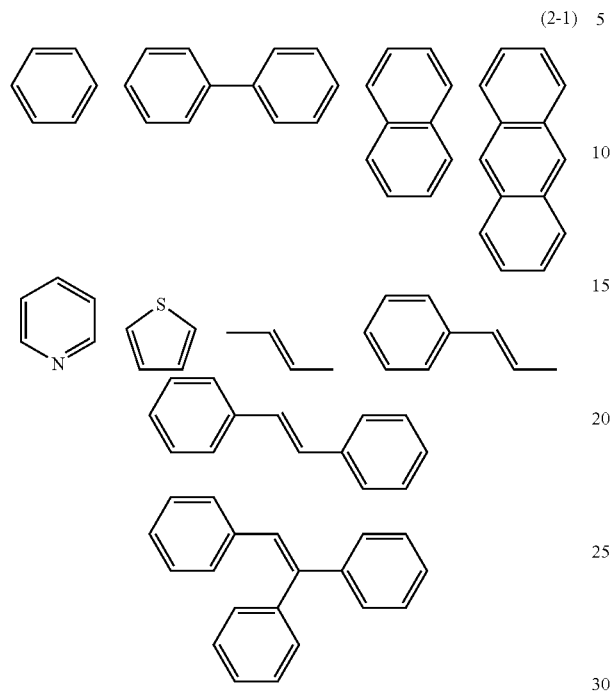

(2-1)

These structures 2-1 are presented merely for the purpose of illustration and are in no way intended to restrict or limit the scope of the invention.

In Formula 1, $R_1$ and $R_2$ are each independently selected from the following structures 2-2:

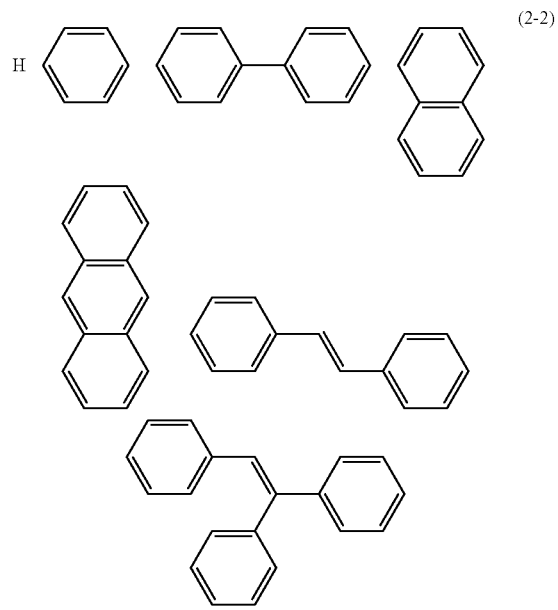

(2-2)

These structures 2-2 are presented merely for the purpose of illustration and are in no way intended to restrict or limit the scope of the invention.

Specific examples of the compound of Formula 1 include the following compounds:

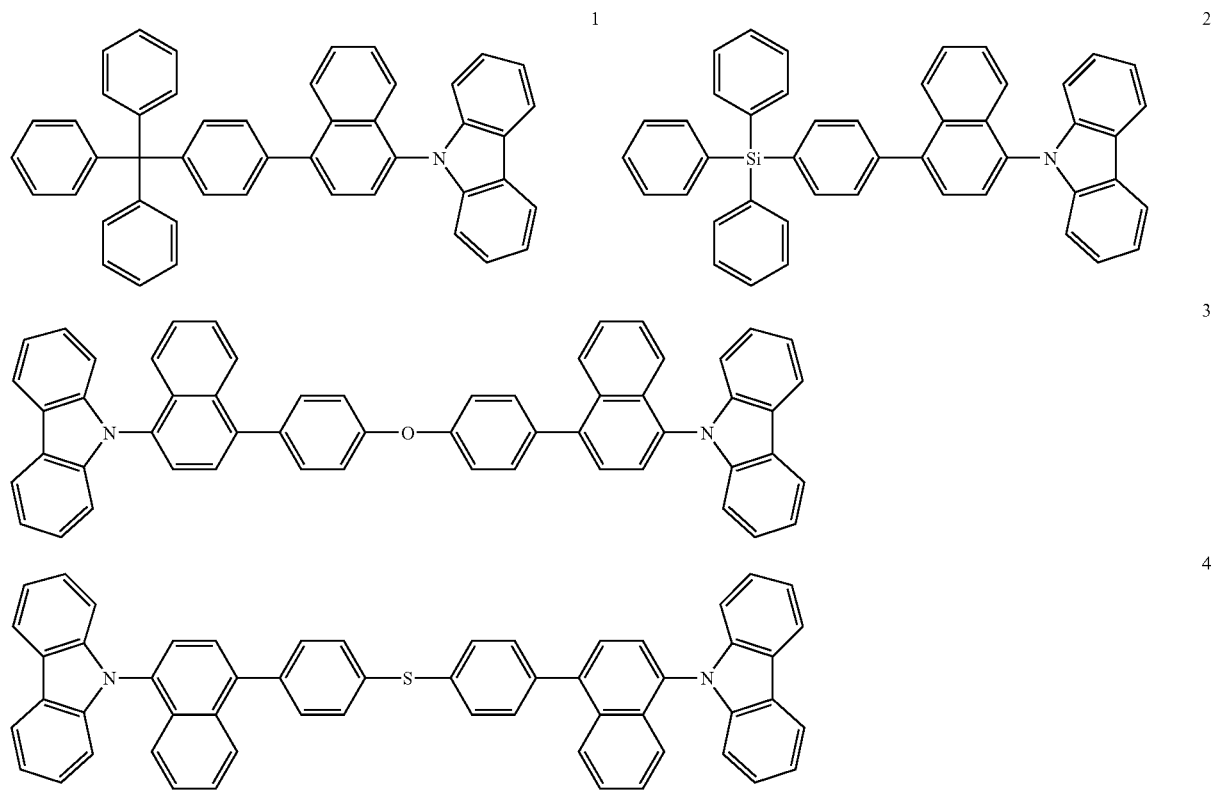

5
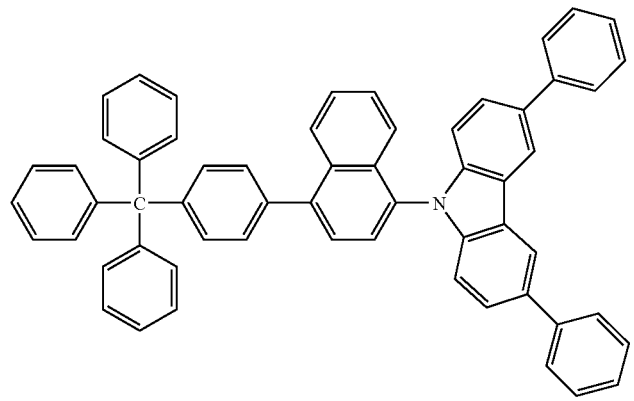
6
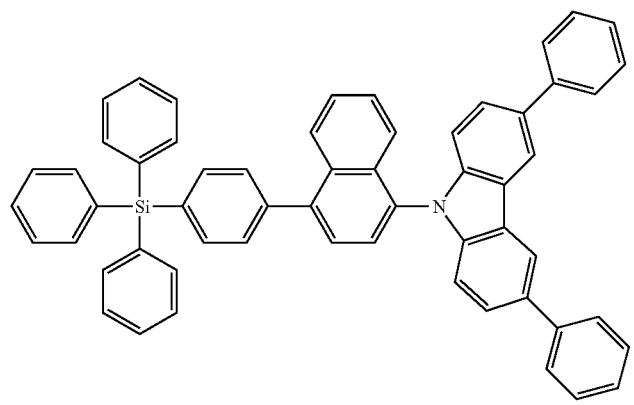
7
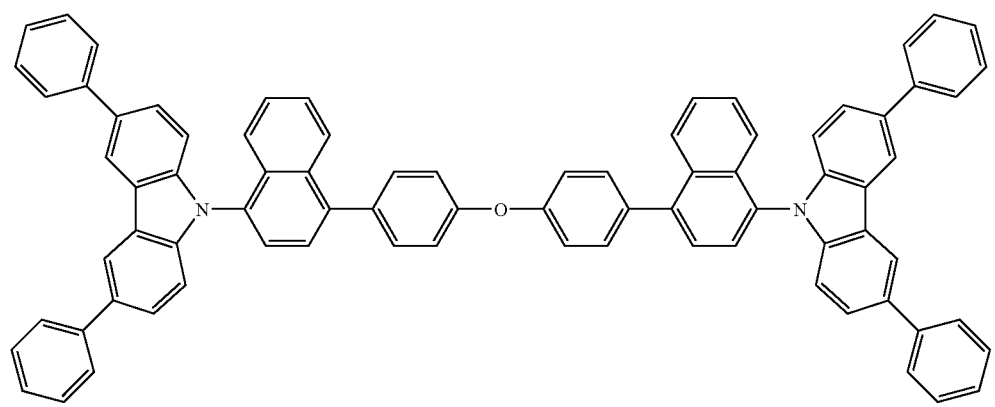
8
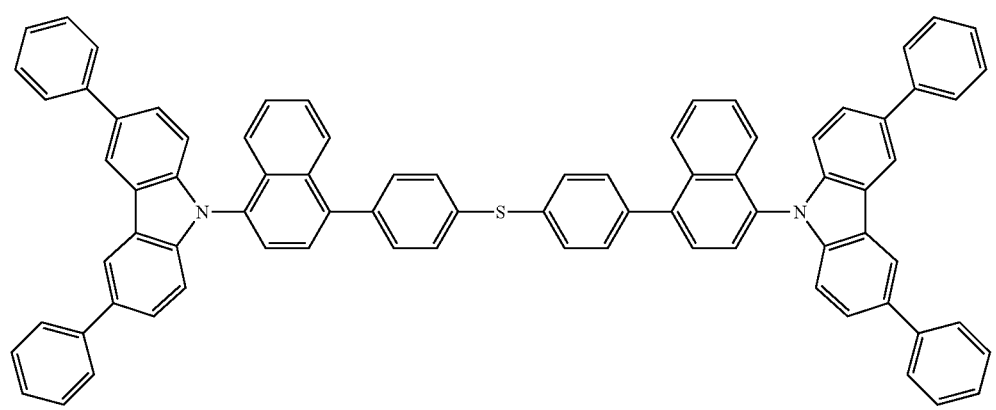

-continued
9
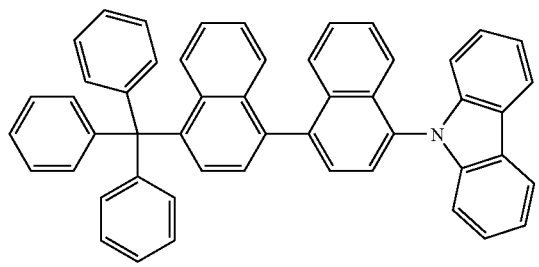
10
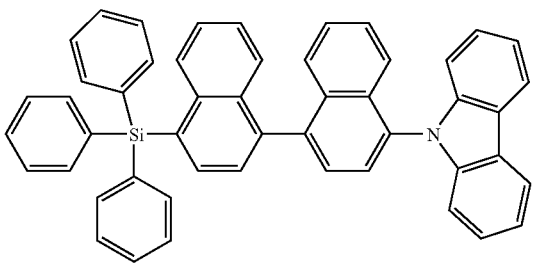
11
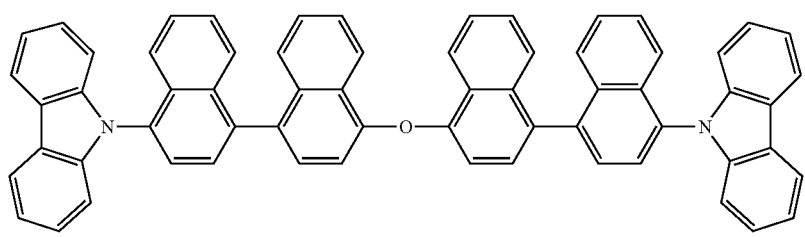
12
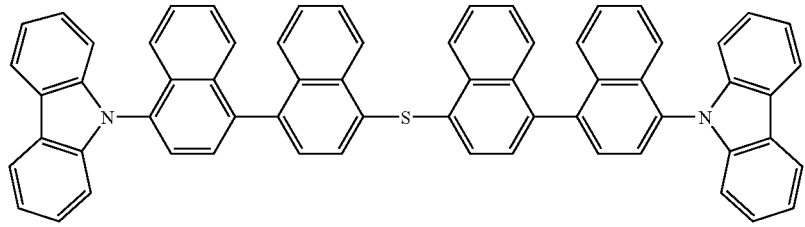
13
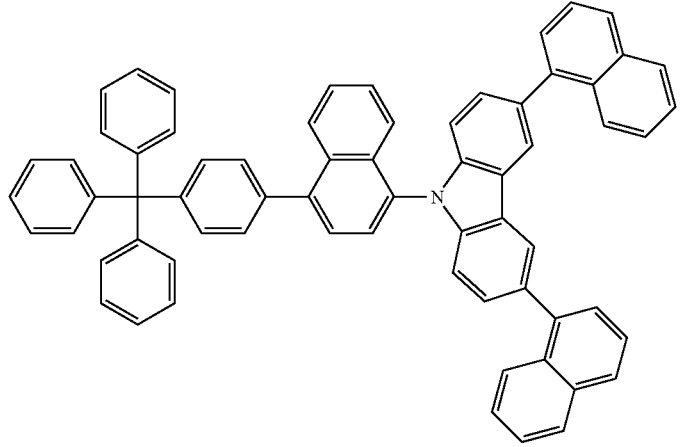
14
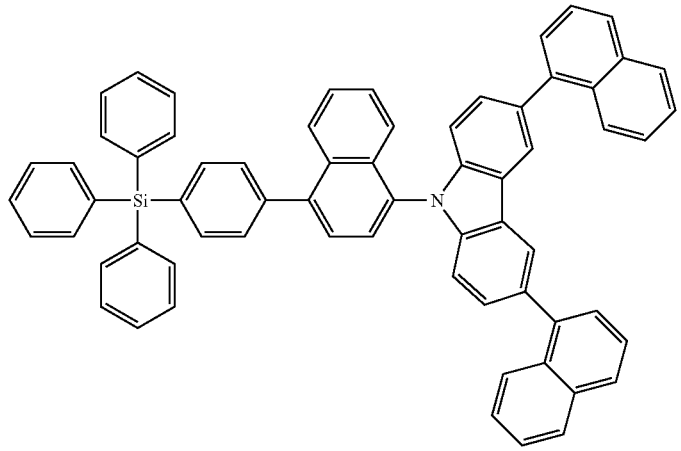

15
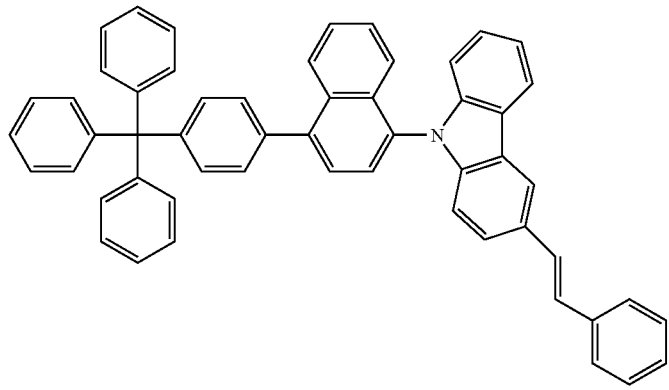
16
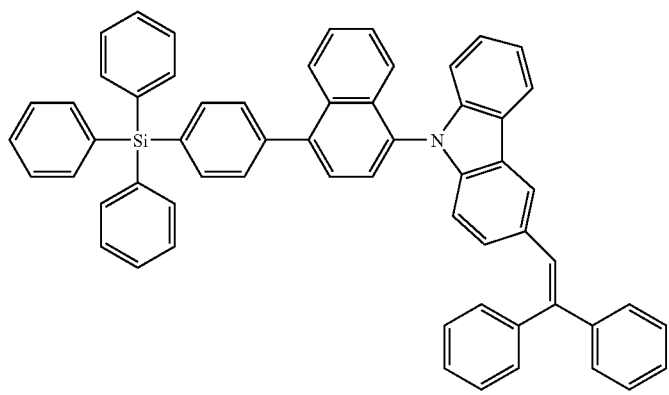
17
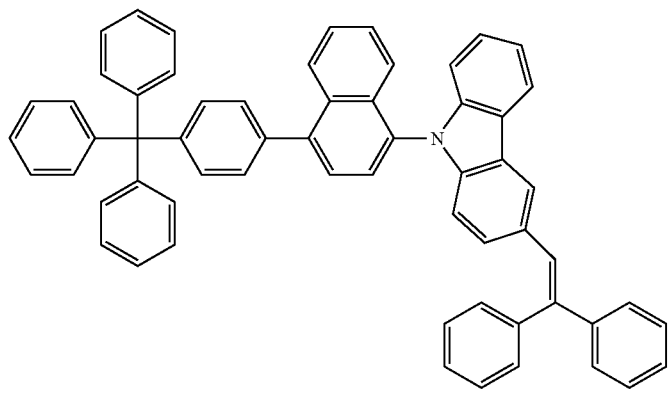
18
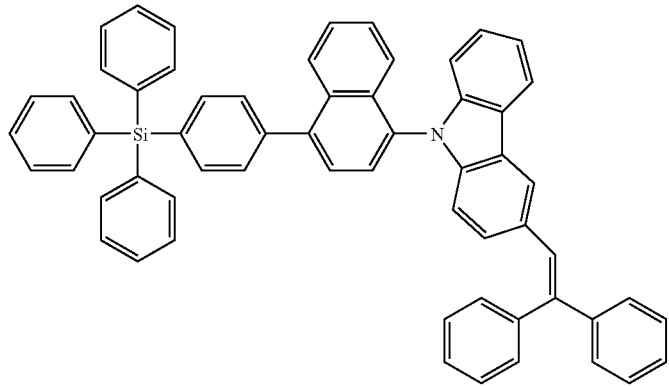

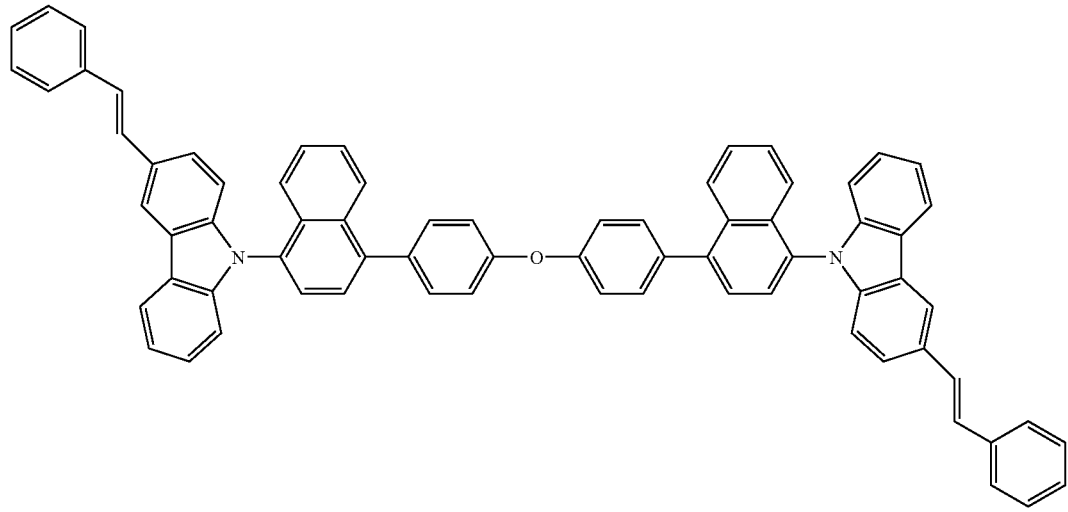
19
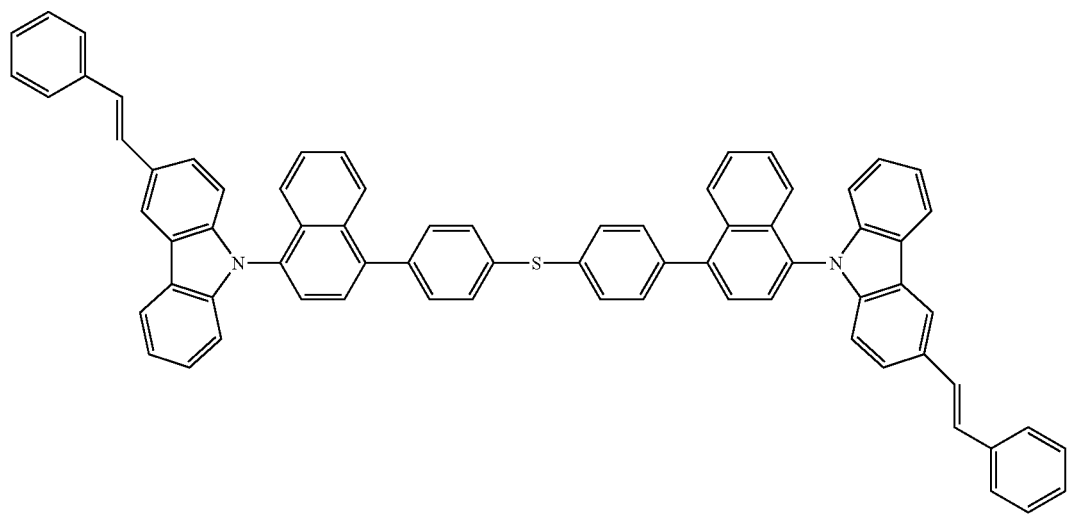
20
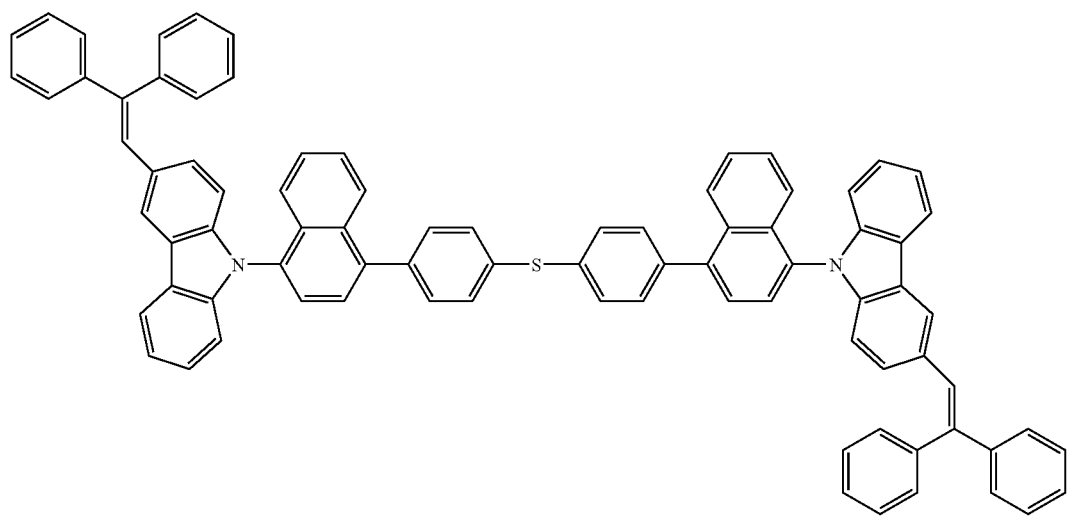
21

21
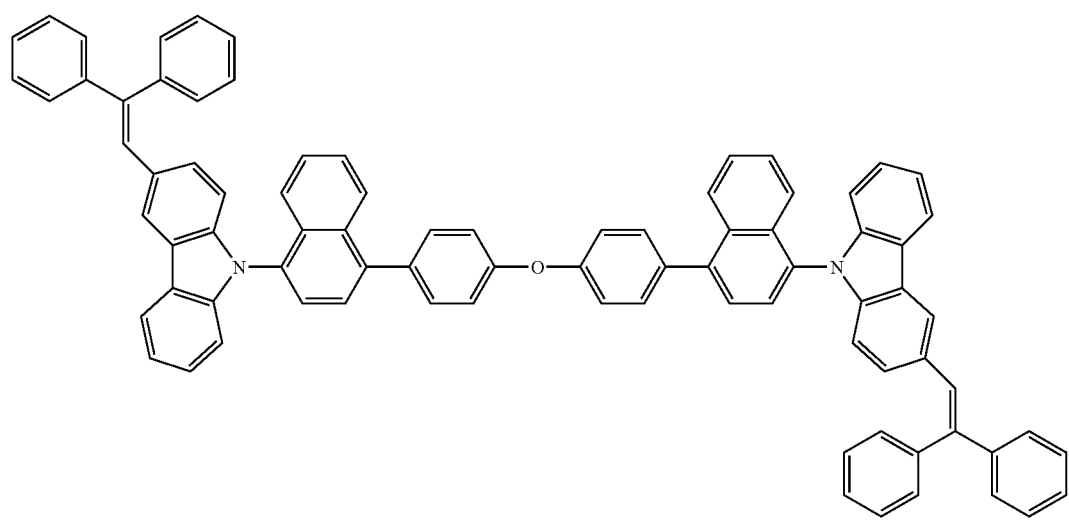
22
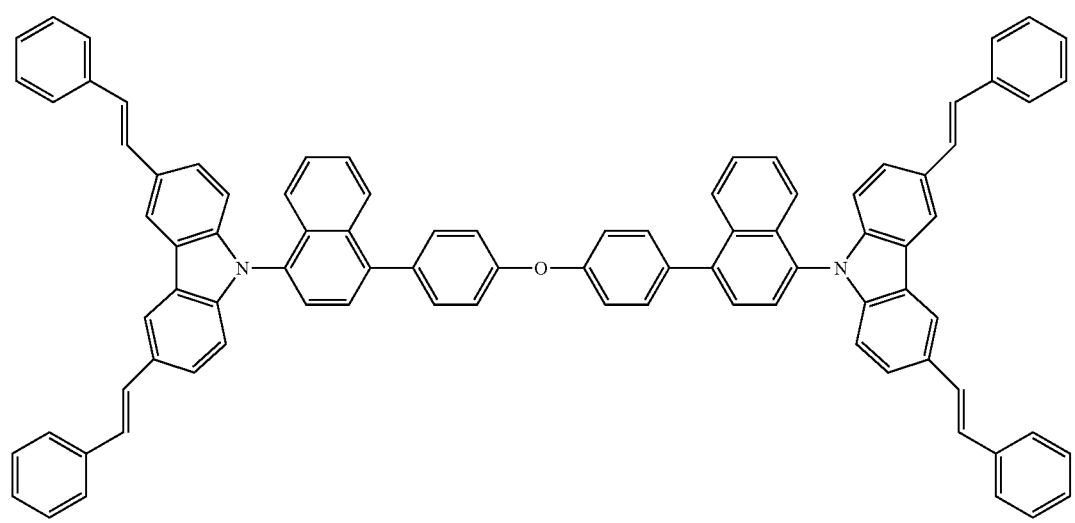
23
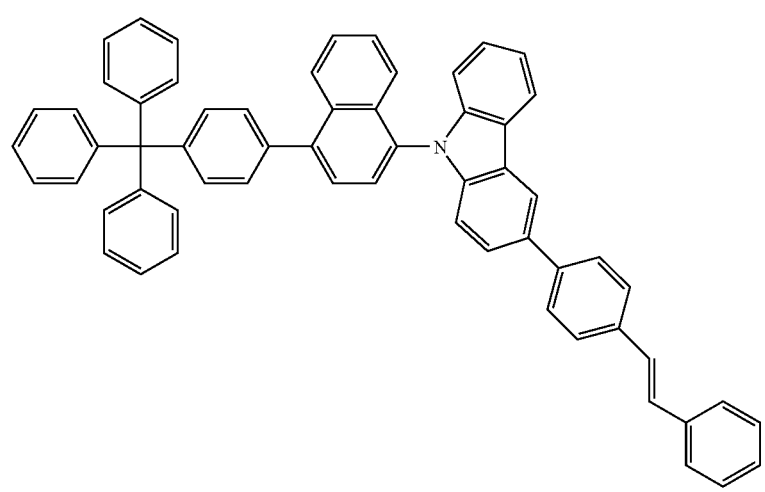
24

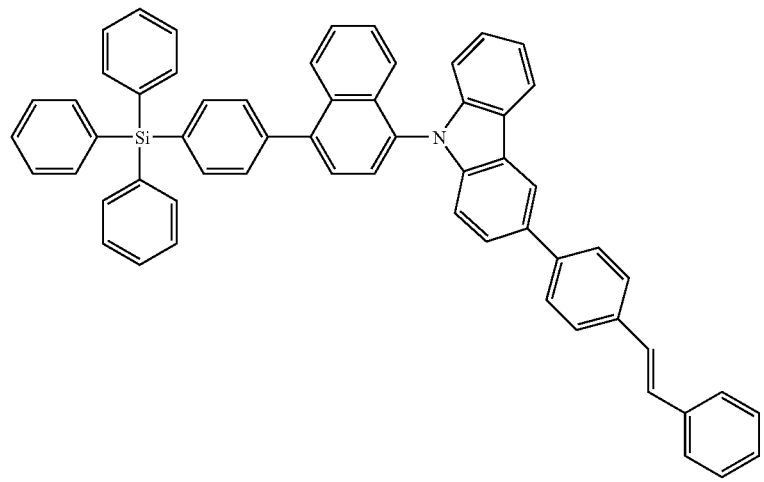
25
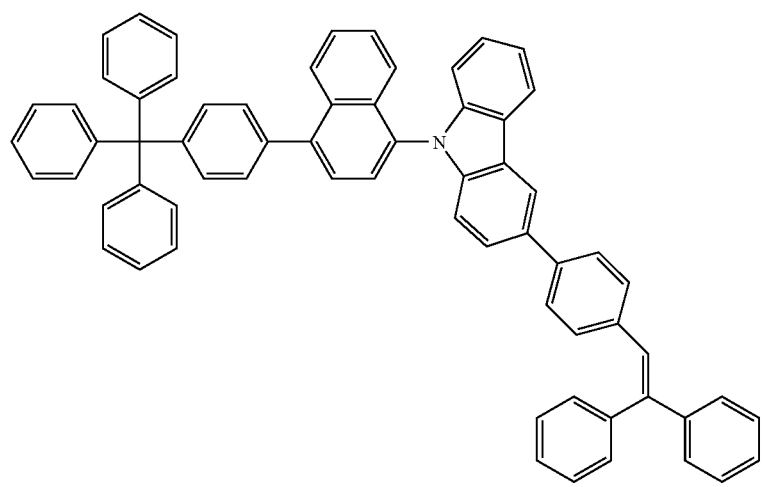
26
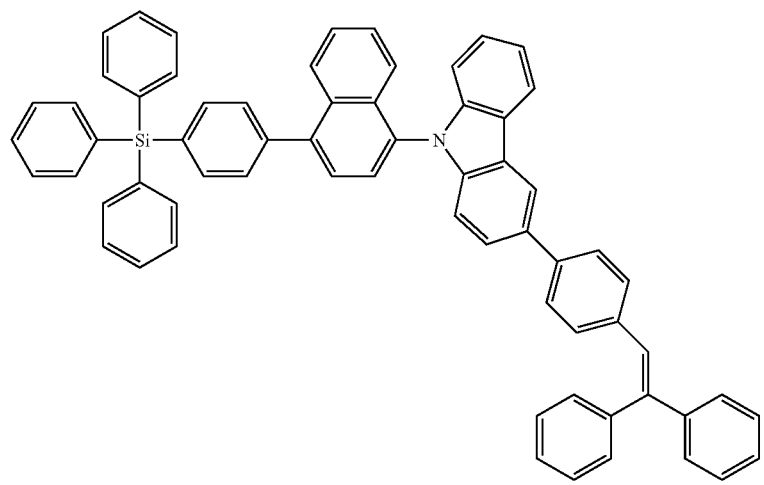
27

-continued
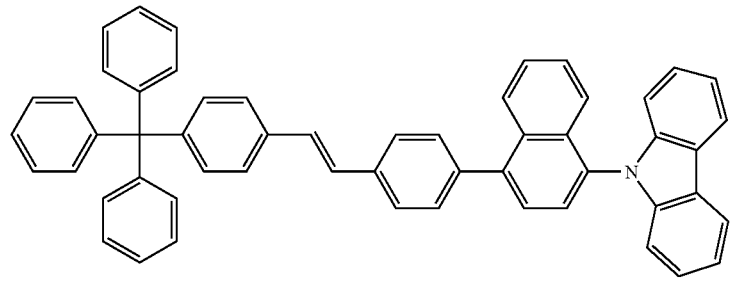
28
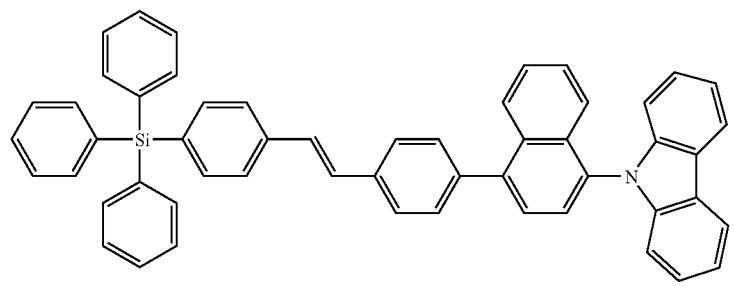
29
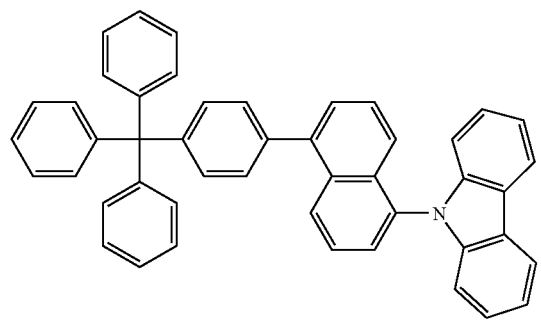
30
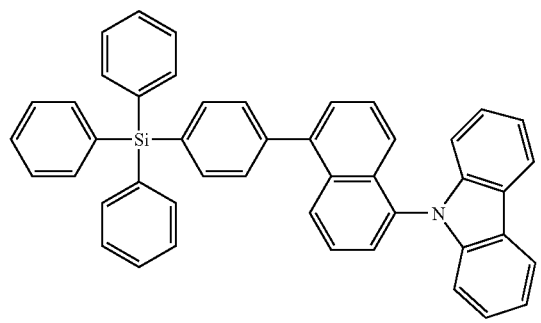
31
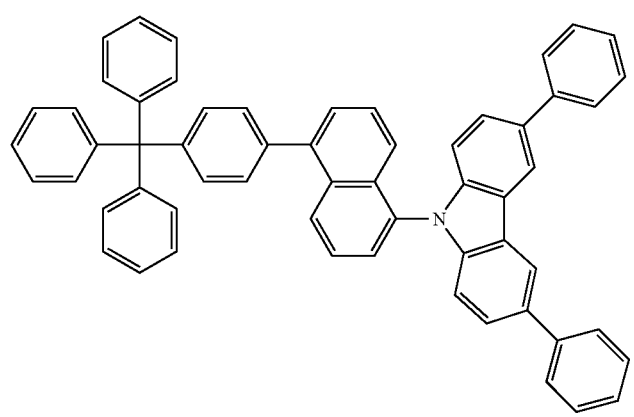
32

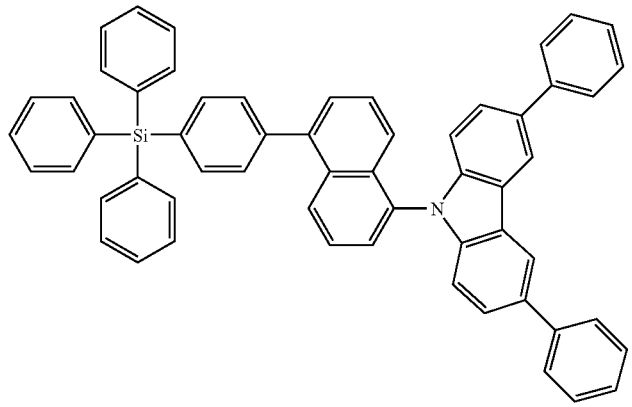

33

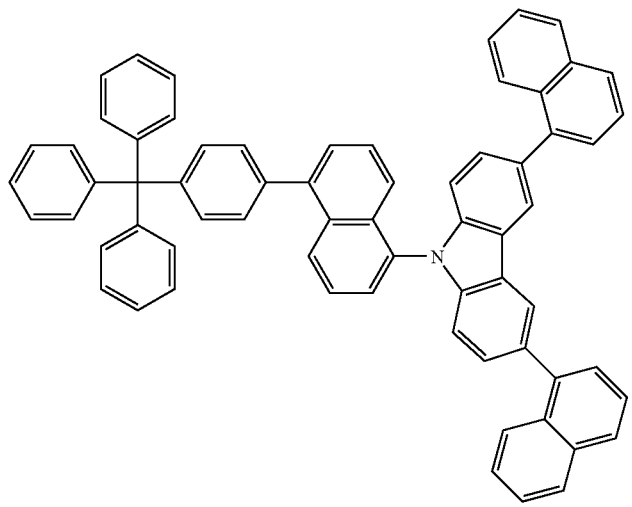

34

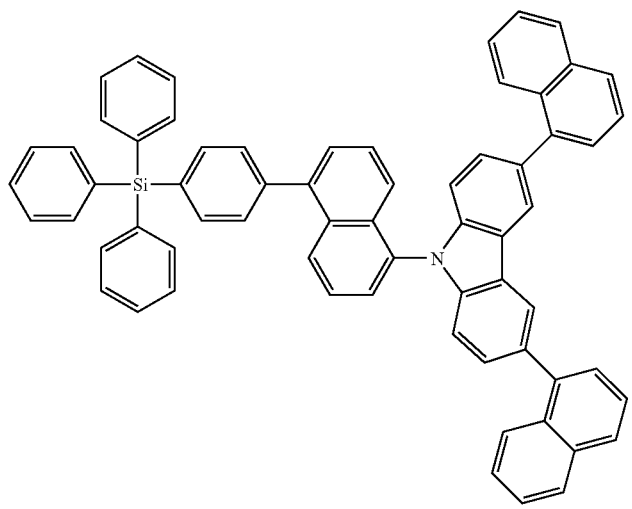

35

These exemplary compounds of the compound of Formula 1 are presented merely for the purpose of illustration and are in no way intended to restrict or limit the scope of the invention.

The present invention also provides an organic electroluminescent device employing the KL host material.

The organic electroluminescent device of the present invention comprises an anode, a cathode and at least one light-emitting layer between the anode and the cathode wherein the light-emitting layer contains the KL host material.

In an embodiment of the present invention, the light-emitting layer contains the KL host material and at least one dopant.

In an embodiment of the present invention, the KL host material may emit light and the dopant may emit light in a single layer.

Figure 4:
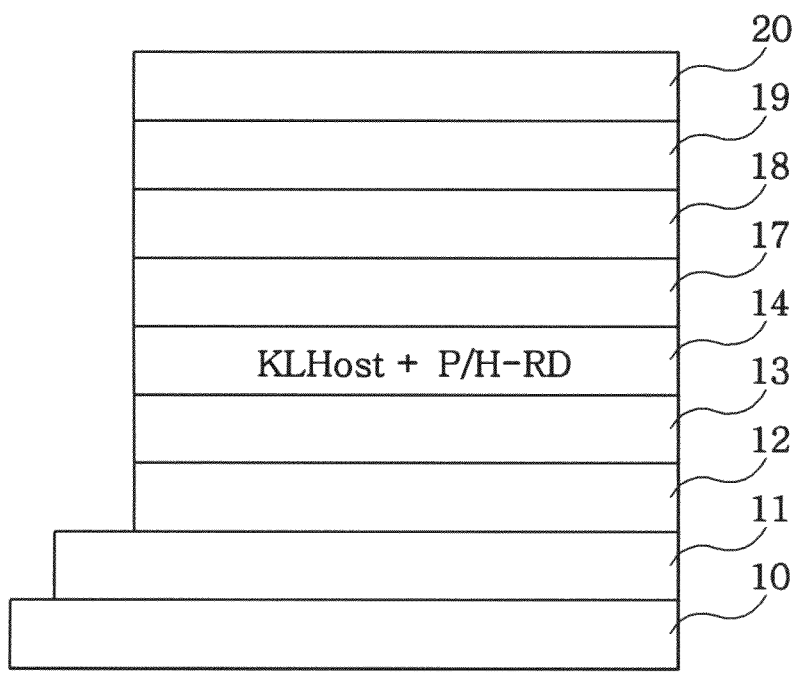
FIG. 4 is a view illustrating the structure of an organic electroluminescent device comprising a light-emitting layer containing a KL host material and a phosphorescent dopant according to an embodiment of the present invention.

FIG. 4 is a schematic view illustrating the structure of an organic electroluminescent device comprising a single light-emitting layer according to an embodiment of the present invention. Specifically, the organic electroluminescent device comprises an anode 11, which is made of indium tin oxide (ITO) by vacuum deposition, a hole injection layer 12, a hole-transporting layer 13, a light-emitting layer, a hole-blocking layer 17, an electron-transporting layer 18, an electron injection layer 19 and a cathode 20 formed in this order on a transparent substrate 10 by vacuum deposition. At least one layer of the hole injection layer, the hole-transporting layer, the hole-blocking layer, the electron-transporting layer and the electron injection layer may be omitted, if desired.

The anode 11 is an electrode that functions to inject holes into the hole injection layer 12. Accordingly, any material capable of imparting the above function to the anode 11 can be used.

Examples of suitable anode materials include: metal oxides and nitrides, such as indium tin oxide (ITO), indium zinc oxide (IZO), tin oxide, zinc oxide, zinc aluminum oxide and titanium nitride; metals, such as gold, platinum, silver, copper, aluminum, nickel, cobalt, lead, molybdenum, tungsten, tantalum and niobium; alloys thereof; alloys of copper iodide; and conductive polymers, such as polyaniline, polythiophene, polypyrrole, polyphenylenevinylene, poly(3-methylthiophene) and polyphenylene. These materials may be used alone or as a mixture of two or more thereof to form the anode 11. The anode 11 may have a multilayer structure including two or more layers of the same or different compositions.

It is preferable that the anode material have a high work function sufficient to facilitate the injection of holes. For example, the work functions of chromium, nickel, gold, palladium, ITO and copper are 4.5 eV, 5.15 eV, 5.1 eV, 5.55 eV, 4.8 eV and 4.65 eV, respectively. The interface between the anode 11 and the hole injection layer 12 preferably has a work function of at least 4 eV.

When the anode 11 is disposed at an end of the device from which light from the light-emitting layer escapes, it is preferable that the anode 11 have a transmittance of not lower than 10% for the light. When the light from the light-emitting layer is in the visible region, ITO is preferably used to form the anode 11 because of its high transmittance in the visible light region.

The hole injection layer 12 is formed of PEDOT/PSS, copper phthalocyanine (CuPc) or 4,4',4"-tris(3-methylphenylphenylamino)triphenylamine (m-MTDATA) and has a thickness of about 5 to 60 nm.

The hole-transporting layer 13 is formed of 4,4'-bis[N-(1-naphthyl)-N-phenyl-amino]-biphenyl (NPD) or N,N'-diphenyl-N,N'-bis(3-methylphenyl)-1,1'-biphenyl -4,4'-diamine (TPD) and has a thickness of about 20 to 60 nm.

The light-emitting layer 14 is characterized by the presence of a KL host material. Any KL host material can be used to form the light-emitting layer 14 so long as it meets the requirements defined above. As a preferable example of the KL host material, there may be exemplified the compound of Formula 1.

In an embodiment of the present invention, when the light-emitting layer 14 has a multilayer structure of two or more layers, the KL host materials of the multilayer structure may be identical to or different from each other.

Figure 5:
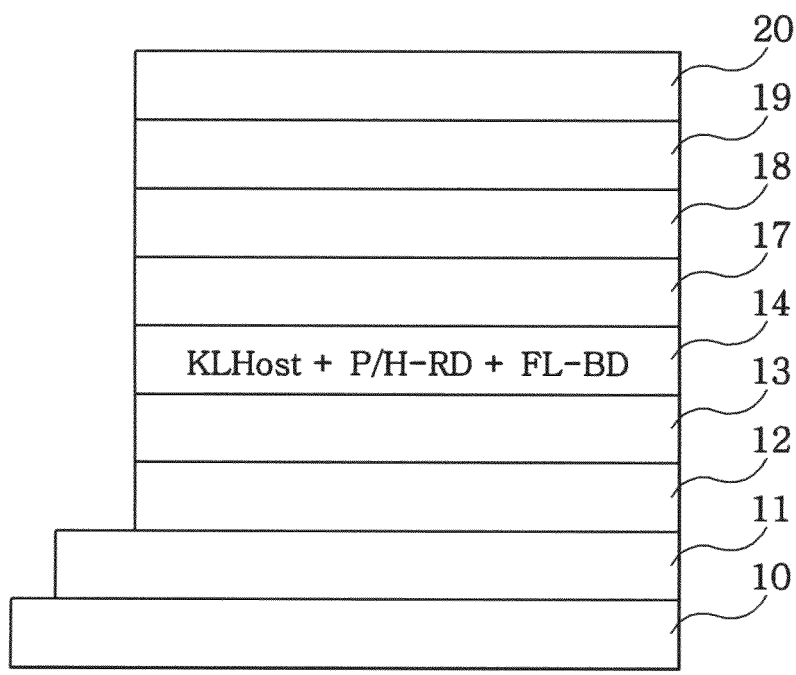
FIG. 5 is a view illustrating the structure of an organic electroluminescent device comprising a light-emitting layer containing a KL host material, a phosphorescent dopant and a fluorescent dopant according to an embodiment of the present invention.

In an embodiment of the present invention, the light-emitting layer may simultaneously emit fluorescence and phosphorescence. Referring to FIG. 5, the KL host material, a phosphorescent dopant and a fluorescent dopant may be present in the light-emitting layer 14.

Figure 6:
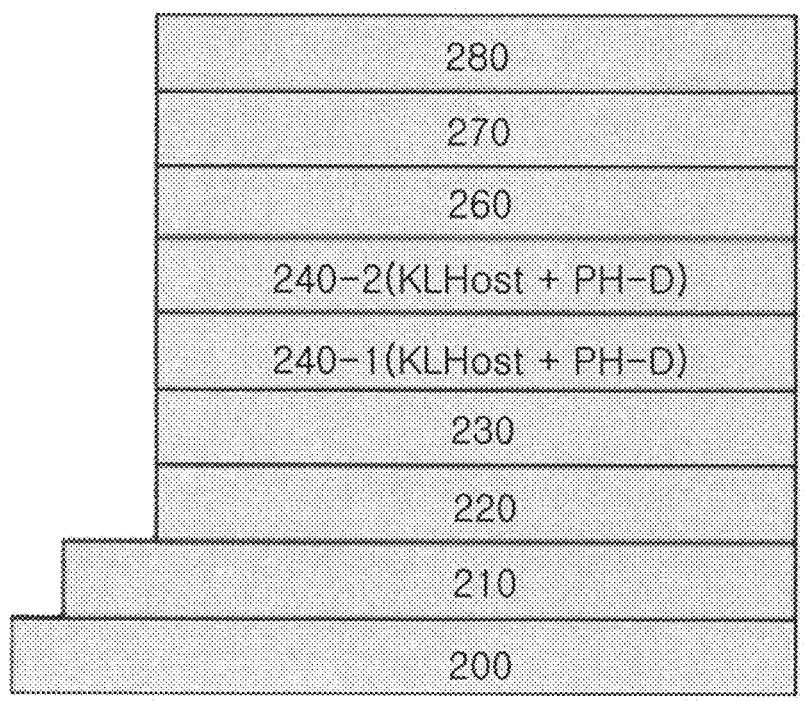
FIG. 6 is a view illustrating the structure of an organic electroluminescent device comprising two light-emitting layers containing a single KL host material and two different phosphorescent dopants according to an embodiment of the present invention.

In an embodiment of the present invention, the light-emitting layer may have a multilayer structure of two or more layers containing the KL host material and different dopants. FIG. 6 shows an organic electroluminescent device comprising a multilayer structure of the light-emitting layer. Referring to FIG. 6, the organic electroluminescent device comprises an anode 210, a hole injection layer 220, a hole-transporting layer 230, a first light-emitting layer 240-1, a second light-emitting layer 240-2, a hole-blocking layer (not shown), an electron-transporting layer 260, an electron injection layer 270 and a cathode 280 formed in this order on a transparent substrate 200 by vacuum deposition. At least one layer of the hole injection layer 220, the hole-transporting layer 230, the hole-blocking layer (not shown), the electron-transporting layer 260 and the electron injection layer 270 may be omitted, if desired.

In an embodiment of the present invention, the light-emitting layer or the multilayer structure of two or more layers may have a thickness of 1 to 60 nm and preferably 10 to 60 nm. If the thickness exceeds 60 nm, an increase in operating voltage and a marked reduction in blue light emission are caused. At least one dopant, preferably two or more different dopants, can be added. There is no particular restriction on the amount of the dopant added. So long as the dopant is added to emit light of its own color, it is meaningless to define the upper limit of the dopant. If desired, a plurality of layers emitting light of different colors can be formed to attain light of various colors by the addition of dopants. Taking advantage of the characteristics of the KL host material such as O, R, G/R, and G/O, a plurality of light-emitting layers, for example, R/G/B, R/G/B/O, can be formed to attain high color reproducibility and high luminance of the device.

In an embodiment of the present invention, when the light-emitting layer has a multilayer structure of two or more layers, the dopants may be different phosphorescent dopants, a phosphorescent dopant and a fluorescent dopant, or different fluorescent dopants. Preferably, the dopants are different phosphorescent dopants.

In an embodiment of the present invention, the dopant may be present in an amount of 0.5 to 35 parts by weight, based on 100 parts by weight of the light-emitting layer. The use of an excessively small amount of the dopant lowers the overall efficiency of the device, making it difficult to use the device. Meanwhile, the use of an excessively large amount of the dopant does not bring about an additional increase in the efficiency of the device above an optimal level, and is thus uneconomical.

In an embodiment of the present invention, light from the KL host material may be mixed with light emitted from the dopant due to the energy transfer of the KL host material. As a result, polychromatic light emission (e.g., white light emission) is achieved or a high-luminance color (e.g., a color of light from the KL host material) can be obtained.

Any fluorescent dopant having an ability to emit fluorescence can be used without particular limitation, and examples thereof include distyrylamine derivatives, pyrene derivatives, perylene derivatives, anthracene derivatives, benzoxazole derivatives, benzothiazole derivatives, benzoimidazole derivatives, chrysene derivatives, phenanthrene derivatives, distyrylbenzene derivatives and tetraphenylbutadiene. An exemplary fluorescent dopant is 4,4'-bis[2-(9-ethylcarbazol-2-yl)vinyl]biphenyl (BCzVBi). Fluorescent dopants sold under the trade marks IDE102 and IDE105 by Idemitsu can also be used.

The phosphorescent dopant is a compound that can emit light from its triplet excitons. The phosphorescent dopant is not particularly limited so long as it can emit light from its triplet excitons. The phosphorescent dopant is preferably a metal complex containing at least one metal selected from the group consisting of Ir, Ru, Pd, Pt, Os and Re. Particularly preferred is a porphyrin metal complex or an ortho-metalated metal complex. As the porphyrin metal complex, a porphyrin platinum complex is preferred.

These phosphorescent dopants may be used singly or in combination of two or more thereof. Various ligands can form ortho-metalated metal complexes. Preferred ligands include 2-phenylpyridine derivatives, 7,8-benzoquinoline derivatives, 2-(2-thienyl)pyridine derivatives, 2-(1-naphthyl)pyridine derivatives and 2-phenylquinoline derivatives. These derivatives can be optionally substituted. Co-ligands, such as acetylacetonate and picric acid, other than the above-mentioned ligands can be further contained. Specific examples of such co-ligands include bisthienylpyridine acetylacetonate iridium, bis(benzothienylpyridine)acetylacetonate iridium, bis(2-phenylbenzothiazole)acetylacetonate iridium, bis(1-phenylisoquinoline)iridium acetylacetonate, tris(1-phenylisoquinoline)iridium, tris(phenylpyridine)iridium, tris(2-phenylpyridine)iridium, tris(3-biphenylpyridine)iridium and tris(4-biphenylpyridine)iridium.

The combined use of the dopant and the KL host material allows for simultaneous emission of light from the dopant and light from the KL host, so that both fluorescence and phosphorescence can be simultaneously emitted from the light-emitting layer. Based on the simultaneous emission of light from the dopant and light from the KL host material, different colors of light from the dopant and the KL host material can be mixed to emit light of various colors, e.g., white color.

In the case where the dopant emitting light of the same color as the KL host material is added, the light from the dopant is mixed with light from the KL host material to achieve high-luminance light emission. As will be described in one of Examples which follow, for example, blue emitting fluorescent/phosphorescent dopants are added to a blue emitting KL host material to achieve high-luminance blue light emission.

The electron-transporting layer can be formed of an aryl-substituted oxadiazole, aryl-substituted triazole, aryl-substituted phenanthroline, benzoxazole or benzothiazole compound. Examples of suitable electron-transporting materials include 1,3-bis(N,N-t-butylphenyl)-1,3,4-oxadiazole (OXD-7), 3-phenyl-4-(1'-naphthyl)-5-phenyl-1,2,4-triazole (TAZ), 2,9-dimethyl-4,7-diphenylphenanthroline (bathocuproine or BCP), bis(2-(2-hydroxyphenyl)-benzoxazolato) zinc, bis(2-(2-hydroxyphenyl)-benzothiazolato) zinc, (4-biphenyl)(4-t-butylphenyl)oxadiazole (PDB) and tris(8-quinolinato)aluminum (III) (Alq3). Preferred is tris(8-quinolinolato)aluminum (III) (Alq3).

Alq3 is typically used to form an electron-transporting layer. In this case, the exciton energy of an adjacent light-emitting material may be transferred to the singlet or triplet of the electron-transporting material. This energy transfer is prevented by the formation of a hole-blocking layer. A material for the hole-blocking layer preferably has an ionization potential greater than that of the light-emitting material, and representative examples thereof include, but are not particularly limited to, biphenoxy-bi(8-quinolinolato) aluminum (BAlq), bathocuproine (BCP) and tris(N-arylbenzimidazole) (TPBI). The hole-blocking layer may have a thickness of about 2 to 20 nm. From the results obtained in Examples which follow, it can be seen that an organic electroluminescent device comprising no hole-blocking layer between the cathode and the light-emitting layer shows higher luminescence efficiency than an organic electroluminescent device comprising a hole-blocking layer. Therefore, the absence of the hole-blocking layer is more desirable. The use of the KL host material eliminates the need for the formation of the hole-blocking layer to reduce the processing time and cost, thus contributing to the slimness of the organic electroluminescent device.

The electron injection layer is formed of LiF. The cathode can be made of a low work function metal, such as Al, Ca or Mg:Ag. Al is preferred.

In an embodiment of the present invention, no hole-blocking layer may be formed between the cathode and the light-emitting layer. According to an alternative embodiment of the present invention, there is provided an organic electroluminescent device comprising a cathode, an electron injection layer, an electron-transporting layer, a light-emitting layer, a hole-transporting layer, a hole injection layer, an anode and a substrate wherein the light-emitting layer contains the KL host material and at least one dopant. The organic electroluminescent device is fabricated without the formation of a hole-blocking layer because the absence of a hole-blocking layer was found to be advantageous in terms of luminescence efficiency.

The present invention also provides a display comprising the organic electroluminescent device.

In an embodiment of the present invention, the display may be a liquid crystal display using a backlight unit. The organic electroluminescent device can be used as a light source of a lighting system. For example, the organic electroluminescent device can find applications as a light source for backlight units of liquid crystal displays and a variety of displays, or a single light source. The display of the present invention may also be an organic electroluminescent display. The organic electroluminescent device of the present invention can also be used in a variety of electric devices. For example, the organic electroluminescent device is combined with color filters in the manufacture of full-color displays.

MODE FOR INVENTION

Hereinafter, the present invention will be explained in more detail with reference to the following examples, including synthesis of the compounds of Formula 1 and fabrication of organic electroluminescent devices.

Synthesis Example 1: Preparation of Compound 2 ("KL-1")

Preparation of 9-(4'-bromonaphthyl)-carbazole

Reaction 1

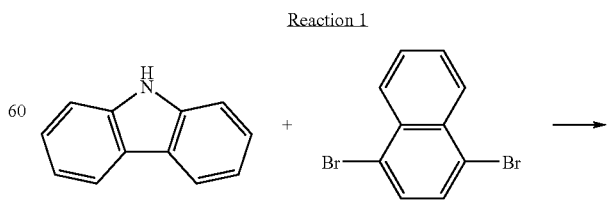

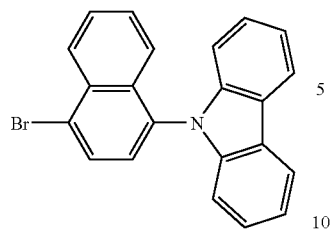

As depicted in Reaction 1, 3.3 g (20 mmol) of carbazole, 8.6 g (40 mmol) of 1,4-dibromonaphthalene, CuI, diaminohexane and $K_3PO_4$ were dissolved in dioxane and refluxed for 15 hours. After completion of the reaction, the reaction mixture was extracted with ethyl acetate. After the solvent was removed under reduced pressure, the residue was purified by column chromatography to give the title compound. The product was collected by filtration under reduced pressure and dried. Yield: 35%. MS (EI) (Calcd. for $C_{22}H_{14}BrN$: 371.03. Found: 371).

Preparation of 4-bromophenyltriphenylsilane

Reaction 2

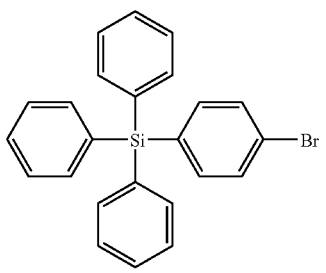

As depicted in Reaction 2, a solution of 4 g (17 mmol) of dibromobenzene in ether was cooled. To the solution were sequentially added n-BuLi and chlorotriphenylsilane. The mixture was allowed to react at room temperature. After completion of the reaction, the reaction mixture was extracted with ether. After the solvent was removed under reduced pressure, the residue was purified by column chromatography to give the title compound. The product was collected by filtration under reduced pressure and dried. Yield: 66%. $^1$H-NMR ($CDCl_3$, ppm): 7.54-7.5 (m, Ar—H), 7.45 (Ar—H), 7.40-7.35 (m, Ar—H). IR (KBr, $cm^{-1}$): 1568, 1477-1376, 1110, 810, 727, 698. MS (EI) (Calcd. for $C_{24}H_{19}BrSi$: 414. Found: 414).

Preparation of 4-phenylboronic acid triphenylsilane

Reaction 3

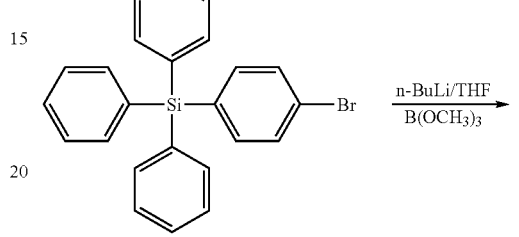

A solution of 8.3 g (20 mol) of 4-bromophenyltriphenylsilane in THF was cooled. To the solution were sequentially added n-BuLi and trimethyl borate. The mixture was allowed to react at room temperature. The reaction mixture was poured into the dilute HCl and stirred for 30 minutes. The resulting mixture was extracted with methylene chloride. After the solvent was removed under reduced pressure, the residue was purified by column chromatography to give the title compound. The product was collected by filtration under reduced pressure and dried. Yield: 50%; $^1$H-NMR ($CDCl_3$): 7.54 (6H, Ar—H), 7.5 (2H, Ar—H), 7.4 (2H, Ar—H), 7.36 (9H, Ar—H), 2.0 (s, 2H, B—$(OH)_2$). IR (KBr, cm-1): 1589, 1491, 1374-1277, 829, 725, 695. MS (EI) (Calcd. for $C_{24}H_{21}BO_2Si$: 380.14. Found: 381)

Preparation of Compound 2

Reaction 4

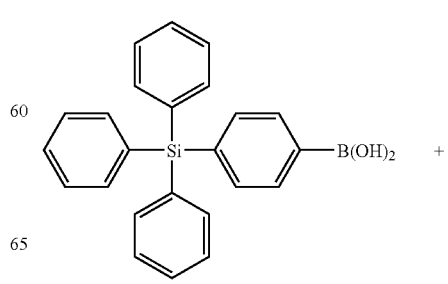

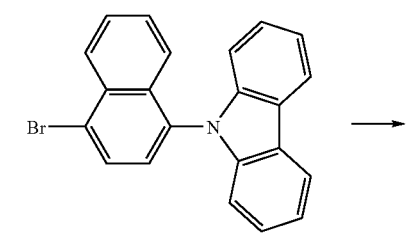

Compound 2

As depicted in Reaction 4, 3.7 g (10 mmol) of 4-bromonaphthylcarbazole, $K_2CO_3$ (2 mol), $Pd(PPh_3)_4$ and toluene were added to 3.8 g (10 mmol) of 4-phenylboronic acid triphenylsilane and refluxed for 10 hours. The reaction mixture was extracted with methylene chloride. The solvent was removed, and then the residue was purified by column chromatography (eluent:hexane) to give Compound 2. Yield: 66%. MS (EI) (Calcd. for $C_{46}H_{33}NSi$: 627.24. Found: 627).

Figure 7:
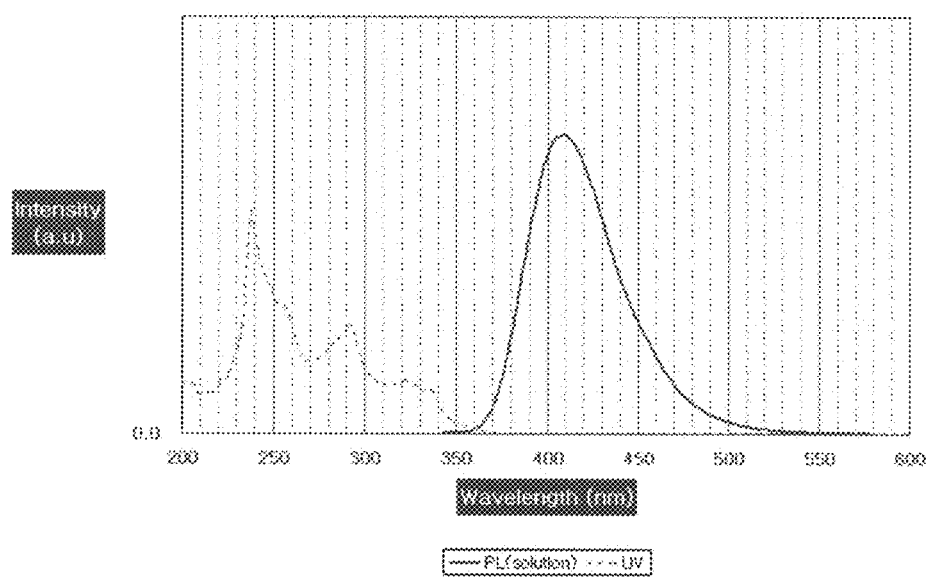
FIG. 7 shows UV emission and photoluminescence (PL) spectra of Compound 2 prepared in Synthesis Example 1.

The UV and PL intensities of Compound 2 are shown in FIG. 7.

Synthesis Example 2: Preparation of Compound 6 ("KL-3")

Preparation of 3,6-diphenylcarbazole

As depicted in Reaction 5, 15 g (46 mmol) of 3,6-dibromocarbazole, 14 g (92 mmol) of phenylboronic acid, $K_2CO_3$ (2 mol), $Pd(PPh_3)_4$ and toluene were refluxed for 10 hours. The reaction mixture was extracted with methylene chloride. The solvent was removed, and then the residue was purified by column chromatography (eluent:hexane) to give the title compound. Yield: 73%. MS (EI) (Calcd. for $C_{24}H_{17}N$, 319.14. Found: 319).

Preparation of 4'-naphthyl-3,6-diphenylcarbazole

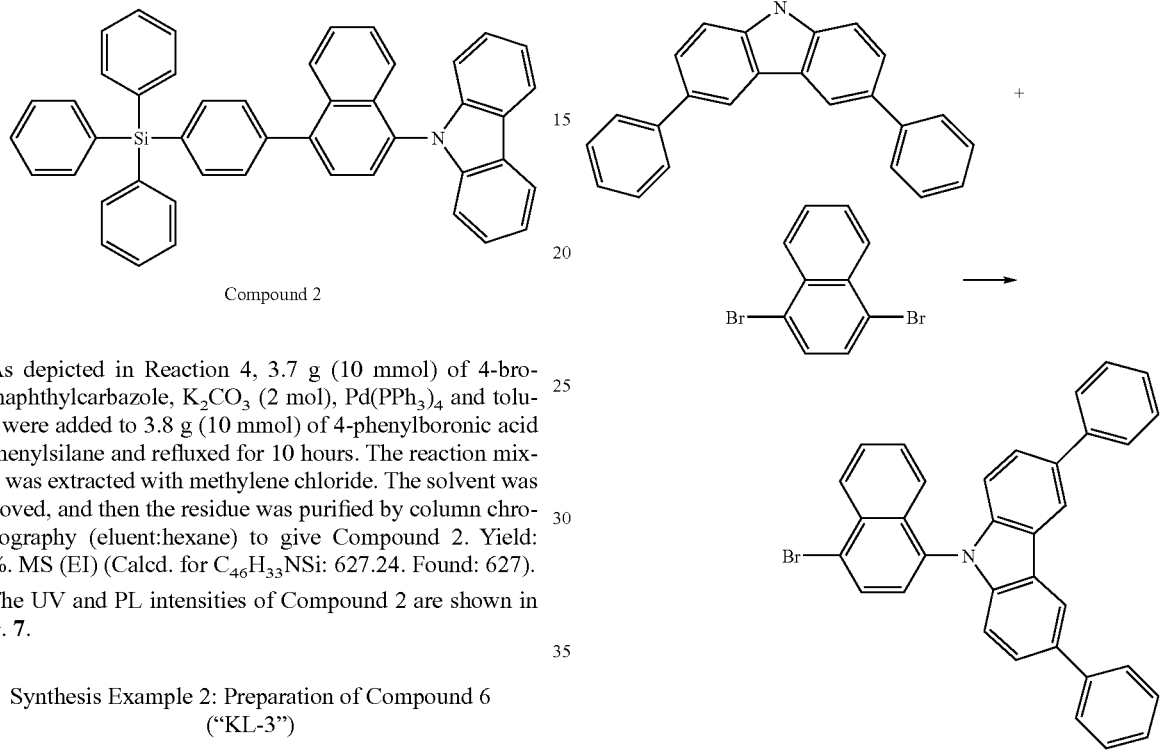

As depicted in Reaction 6, a solution of 10 g (31.3 mmol) of carbazole, 13.5 g (31.3 mmol) of 1,4-dibromonaphthalene, CuI, diaminohexane and $K_3PO_4$ in dioxane was refluxed for 15 hours. After completion of the reaction, the reaction mixture was extracted with ethyl acetate. After the solvent was removed under reduced pressure, the residue was purified by column chromatography to give the title compound. The product was collected by filtration under reduced pressure and dried. Yield: 6%. MS (EI) (Calcd. for $C_{34}H_{22}BrN$: 523.09. Found: 523).

Preparation of Compound 6

-continued

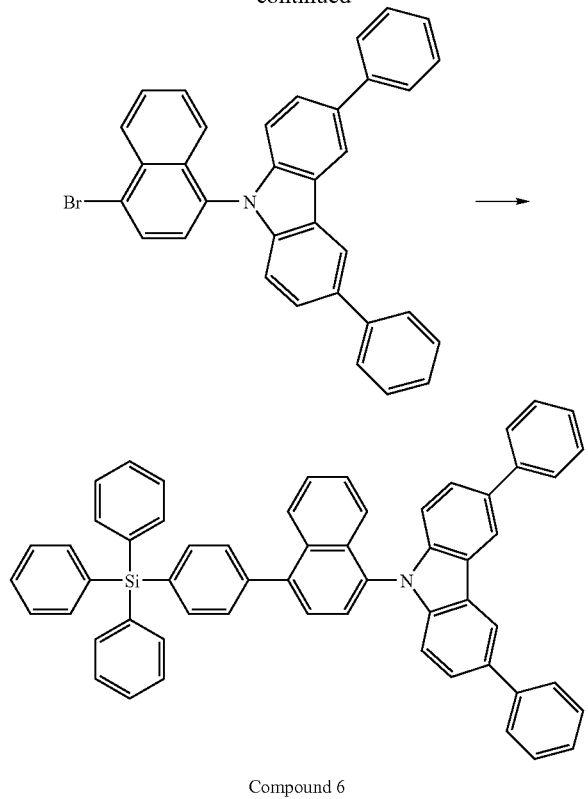

Compound 6

As depicted in Reaction 7, 1.7 g (3.3 mmol) of 4-bromonaphthyl-3,6-diphenylcarbazole, $K_2CO_3$ (2 mol), $Pd(PPh_3)_4$ and toluene were added to 2 g (3.3 mmol) of 4-phenylboronic acid triphenylsilane and refluxed for 10 hours. The reaction mixture was extracted with methylene chloride. The solvent was removed, and then the residue was purified by column chromatography (eluent: hexane) to give Compound 6. Yield: 95.6%. MS (EI) (Calcd. for $C_{58}H_{41}NSi$: 779.3. Found: 779.7).

Figure 8:
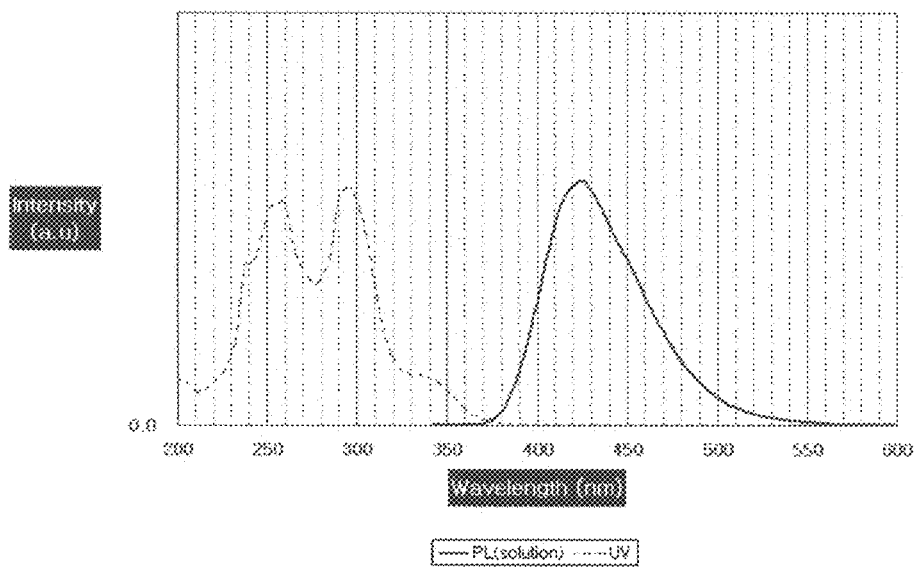
FIG. 8 shows UV emission and photoluminescence (PL) spectra of Compound 6 prepared in Synthesis Example 2.

The UV and PL intensities of Compound 6 are shown in FIG. 8.

[Fabrication of Organic Electroluminescent Devices]

Example 1: Fabrication of Organic Electroluminescent Device

Figure 13:
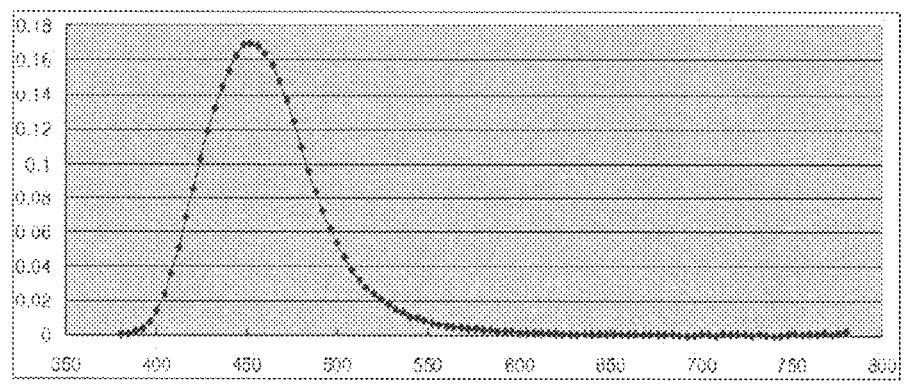
FIG. 13 is an EL spectrum of an organic electroluminescent device fabricated in Example 1.

A substrate (Asahi Glass Co. Ltd.), which is a glass substrate 100 deposited with ITO as an anode material 110, was prepared as a unit device. The ITO-deposited glass substrate 100 was patterned by lithography. The patterned unit substrate was pretreated by sequential cleaning with acetone, a detergent, distilled water and isopropyl alcohol, followed by $UV/O_3$ cleaning and plasma treatment. The surface-treated substrate was transferred to a glass chamber. In the glass chamber, m-MTDATA, NPD, KL-1 (Compound 2), BAlq and Alq3 were sequentially deposited to thicknesses 50, 20, 30, 10 and 20 nm on the surface-treated substrate to form a hole injection layer, a hole-transporting layer, a light-emitting layer, a hole-blocking layer and an electron-transporting layer, respectively. After the deposition of the organic layers was finished, the resulting structure was transferred to a metal chamber, where an electron injection layer and a cathode were sequentially formed thereon. Encapsulation was performed without using a getter in a glove box to fabricate an organic electroluminescent device. See, FIG. 13 and Table 2.

Example 2: Fabrication of Organic Electroluminescent Device

Figure 14:
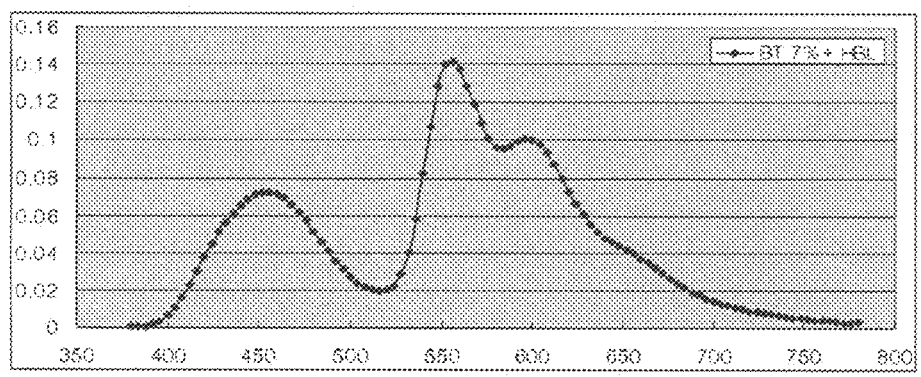
FIG. 14 is an EL spectrum of an organic electroluminescent device (Example 2) comprising a hole-blocking layer and employing a phosphorescent dopant and a host material.

An organic electroluminescent device was fabricated in the same manner as in Example 1 except that $Ir(bt)_2(acac)$ (7%) as a phosphorescent dopant was deposited to form a light-emitting layer. See, FIG. 14 and Table 2.

Example 3: Fabrication of Organic Electroluminescent Device

An organic electroluminescent device was fabricated in the same manner as in Example 1 except that the fluorescent dopant (1%) of Formula 3 was doped to form a light-emitting layer. See, Table 3.

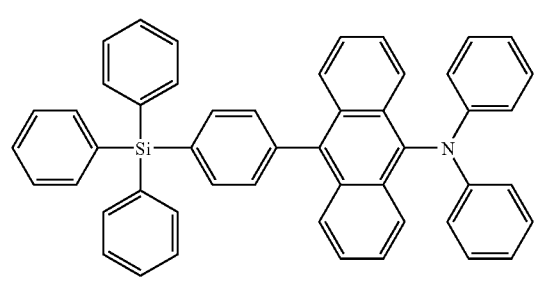

(3)

Example 4: Fabrication of Organic Electroluminescent Device

An organic electroluminescent device was fabricated in the same manner as in Example 1 except that KL-3 (Compound 6) was used as a host material instead of KL-1 (Compound 2) and $Ir(bt)_2(acac)$ (7%) as a phosphorescent dopant was deposited to form a light-emitting layer. See, Table 4.

Example 5: Fabrication of Organic Electroluminescent Device (M/L-1-BCP)

Figure 15:
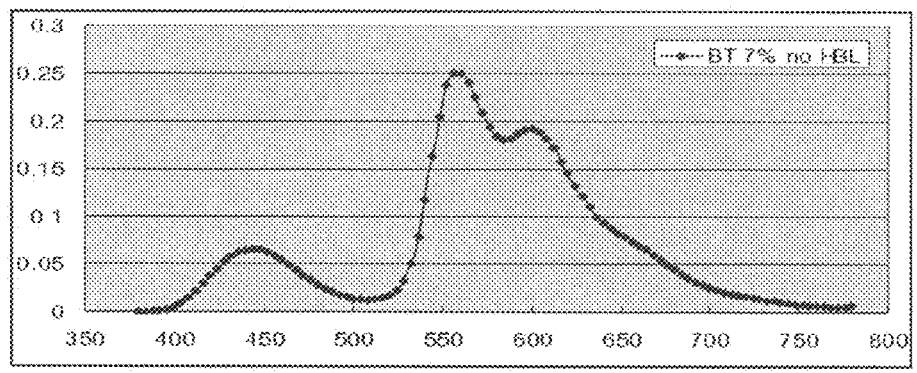
FIG. 15 is an EL spectrum of an organic electroluminescent device (Example 5) comprising no hole-blocking layer and employing a phosphorescent dopant and a host material.

An organic electroluminescent device was fabricated in the same manner as in Example 2 except that BCP and Alq3 were deposited to thicknesses of 10 nm and 20 nm to form a hole-blocking layer and an electron-transporting layer, respectively. See, FIG. 15 and Table 5.

Example 6: Fabrication of Organic Electroluminescent Device (KLhost-1 BD, RD-Doping)

An organic electroluminescent device was fabricated in the same manner as in Example 2 except that the light-emitting layer was deposited with KLhost-1 (30 nm), the fluorescent dopant (1 wt %) of Formula 3 and $Ir(bt)_2(acac)$ (7 wt %) as a phosphorescent dopant by doping. See, Table 6.

Example 7: Fabrication of Organic Electroluminescent Device (M/L-1)

An organic electroluminescent device was fabricated in the same manner as in Example 2 except that the thickness of the light-emitting layer was changed to 40 nm and the formation of the hole-blocking layer was omitted. See, Table 7.

Example 8: Fabrication of Organic Electroluminescent Devices [KL-1 (40 nm) BT (3, 5, 7 and 10 wt %)]

Figure 16:
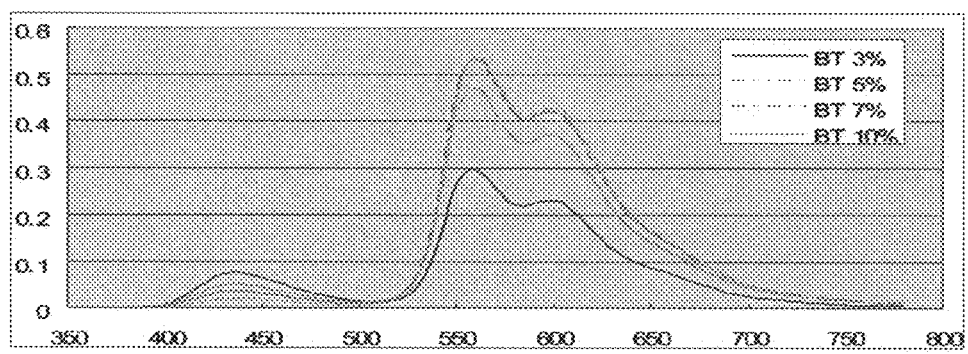
FIG. 16 is a graph showing variations in the luminescence intensity of an organic electroluminescent device (Example 8) employing a yellow phosphorescent dopant at various doping concentrations.

Organic electroluminescent devices were fabricated in the same manner as in Example 7 except that BT as a phosphorescent dopant was deposited at different concentrations (3, 5, 7 and 10 wt %). Table 8 shows the results obtained when BT was used at concentrations of 3, 5, 7 and 10 wt %. See, FIG. 16.

Example 9: Fabrication of Organic Electroluminescent Devices [KL-1 (40 nm) Bzq (3, 5, 7 and 10 wt %)]

Figure 17:
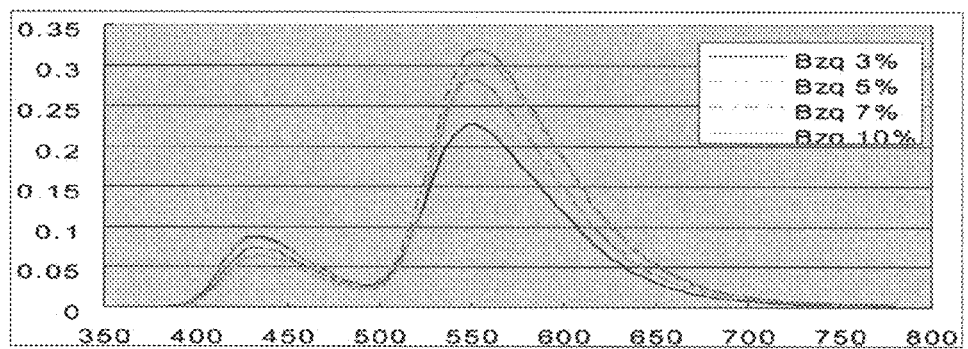
FIG. 17 is a graph showing variations in the luminescence intensity of an organic electroluminescent device (Example 9) employing a green phosphorescent dopant at various doping concentrations.
Figure 18:
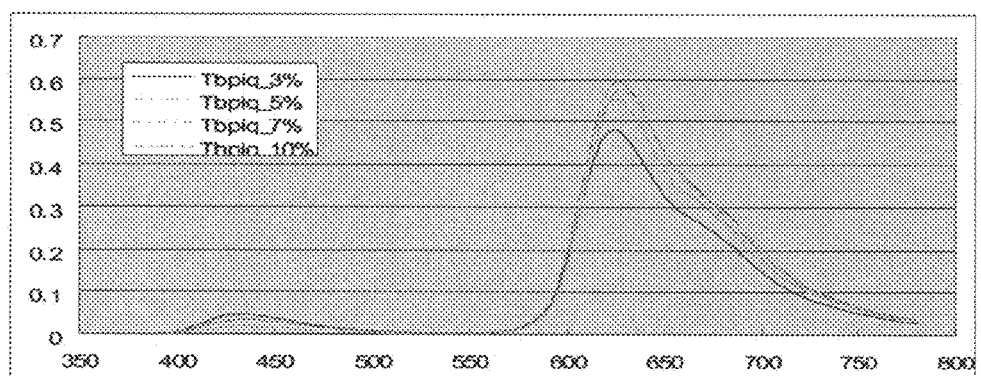
FIG. 18 is a graph showing variations in the luminescence intensity of an organic electroluminescent device (Example 10) employing a red phosphorescent dopant at various doping concentrations.
Figure 19:
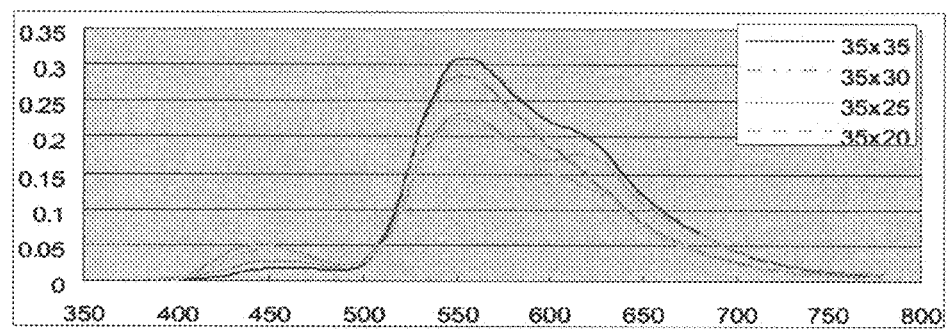
FIG. 19 is a graph showing variations in the luminescence intensity of an organic electroluminescent device (Example 11) comprising a red phosphorescent layer and a green phosphorescent layer when the thickness of the red phosphorescent layer was set to 35 nm and the thickness of the green phosphorescent layer was varied.
Figure 20:
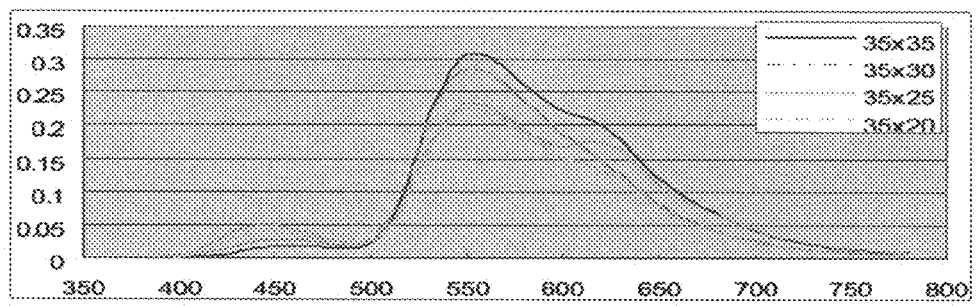
FIG. 20 is a graph showing variations in the luminescence intensity of an organic electroluminescent device (Example 11) comprising a red phosphorescent layer and a green phosphorescent layer when the thickness of the red phosphorescent layer was set to 30 nm and the thickness of the green phosphorescent layer was varied.
Figure 21:
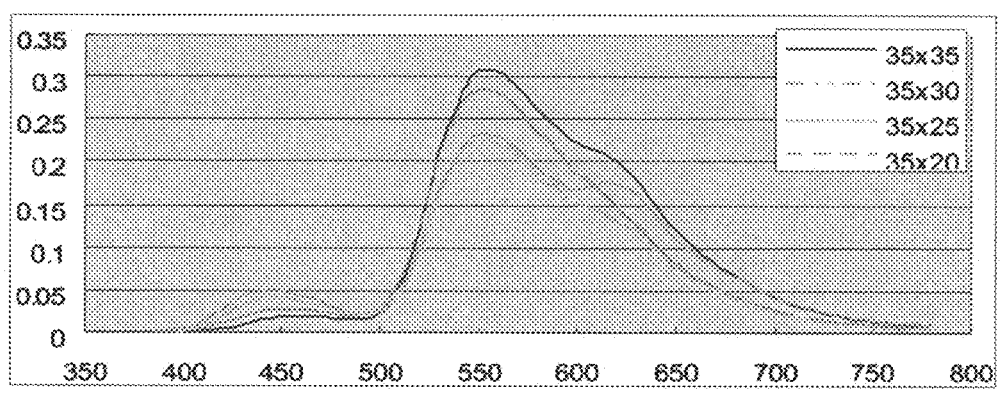
FIG. 21 is a graph showing variations in the luminescence intensity of an organic electroluminescent device (Example 11) comprising a red phosphorescent layer and a green phosphorescent layer when the thickness of the red phosphorescent layer was set to 25 nm and the thickness of the green phosphorescent layer was varied.
Figure 22:
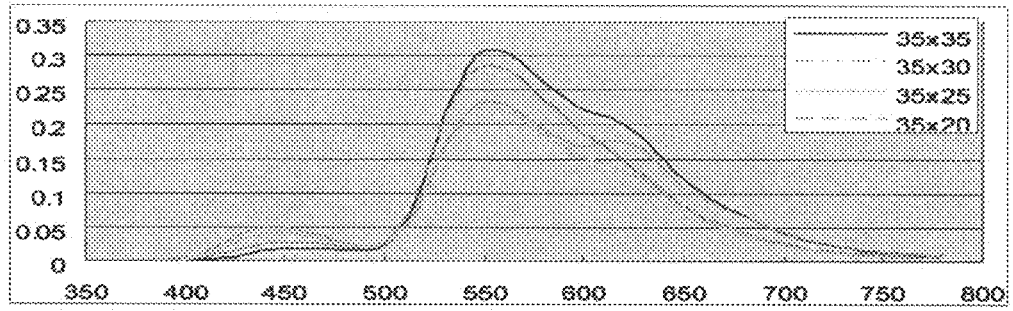
FIG. 22 is a graph showing variations in the luminescence intensity of an organic electroluminescent device (Example 11) comprising a red phosphorescent layer and a green phosphorescent layer when the thickness of the red phosphorescent layer was set to 20 nm and the thickness of the green phosphorescent layer was varied.
Figure 23:
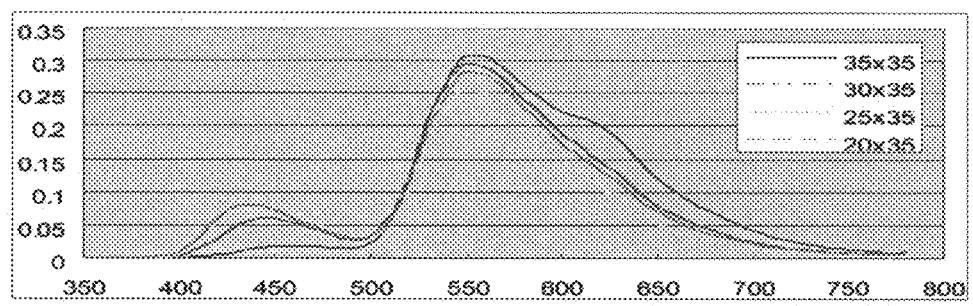
FIG. 23 is a graph showing variations in the luminescence intensity of an organic electroluminescent device (Example 11) comprising a red phosphorescent layer and a green phosphorescent layer when the thickness of the green phosphorescent layer was set to 35 nm and the thickness of the red phosphorescent layer was varied.
Figure 24:
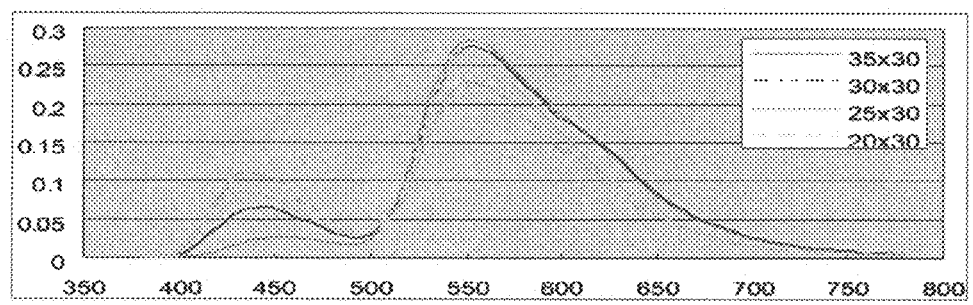
FIG. 24 is a graph showing variations in the luminescence intensity of an organic electroluminescent device (Example 11) comprising a red phosphorescent layer and a green phosphorescent layer when the thickness of the green phosphorescent layer was set to 30 nm and the thickness of the red phosphorescent layer was varied.
Figure 25:
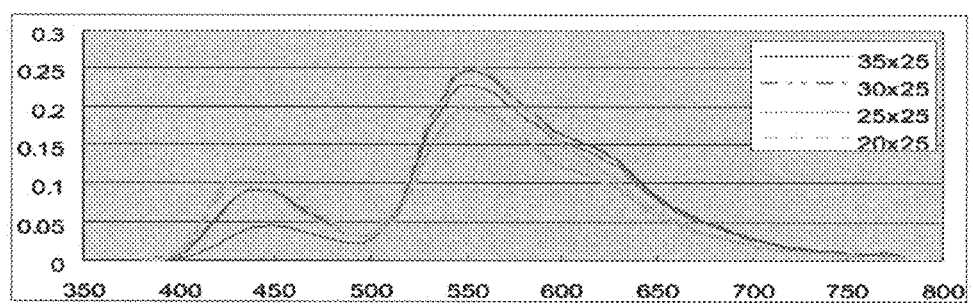
FIG. 25 is a graph showing variations in the luminescence intensity of an organic electroluminescent device (Example 11) comprising a red phosphorescent layer and a green phosphorescent layer when the thickness of the green phosphorescent layer was set to 25 nm and the thickness of the red phosphorescent layer was varied.
Figure 26:
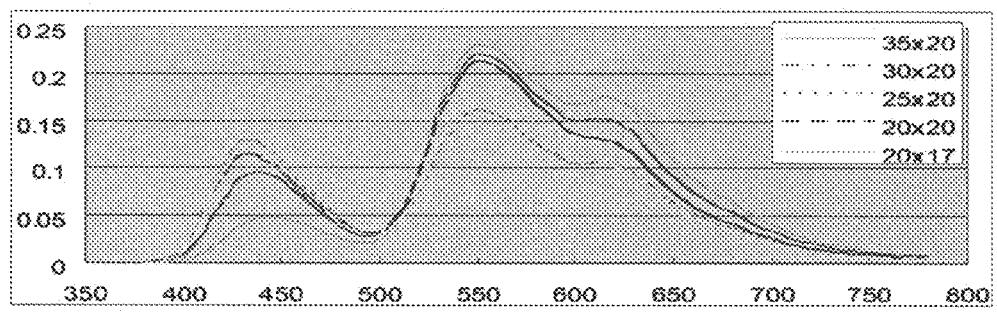
FIG. 26 is a graph showing variations in the luminescence intensity of an organic electroluminescent device (Example 11) comprising a red phosphorescent layer and a green phosphorescent layer when the thickness of the green phosphorescent layer was set to 20 nm or 17 nm and the thickness of the red phosphorescent layer was varied.

Organic electroluminescent devices were fabricated in the same manner as in Example 7 except that iridium (III) bis(7, 8-benzoquinoline)acetylacetonate (Bzq) as a phosphorescent dopant was deposited at different concentrations (3, 5, 7 and 10 wt %). Table 9 shows the results obtained when Bzq was used at concentrations of 3, 5, 7 and 10 wt %. See, FIG. 17.

Example 10: Fabrication of Organic Electroluminescent Devices [KL-1 (40 nm) Tbpiq (3, 5, 7 and 10 wt %)]

Organic electroluminescent devices were fabricated in the same manner as in Example 7 except that iridium (III) bis(1-(4-tert-butylphenyl)isoquinoline)acetylacetonate (Tbpiq) as a phosphorescent dopant was deposited at different concentrations (3, 5, 7 and 10 wt %). Table 10 shows the results obtained when Tbpiq was used at concentrations of 3, 5, 7 and 10 wt %. See, FIG. 17.

Example 11: Fabrication of Organic Electroluminescent Devices [KL -1 Bzq (6%)/Tbpiq (7%)/]

Organic electroluminescent devices were fabricated in the same manner as in Example 7 except that Bzq as a green phosphorescent and Tbpiq as a red phosphorescent dopant were sequentially laminated to various thicknesses ranging from 35 nm×35 nm to 25 nm×20 nm by doping to form two light-emitting layers. At this time, the green and red dopants were deposited at concentrations of 6 wt % and 7 wt % by doping, respectively. See, FIGS. 19-26 and Table 11. In Table 11, for example, 35×35 indicates that Bzq (6%) and Tbpiq (7%) were laminated to thicknesses of 35 nm and 35 nm, respectively.

Example 12: Fabrication of Organic Electroluminescent Devices [KL-1 (40 nm) Ir(ppy)$_3$ (3%, 5%, 7% and 10 wt %)]

Figure 27:
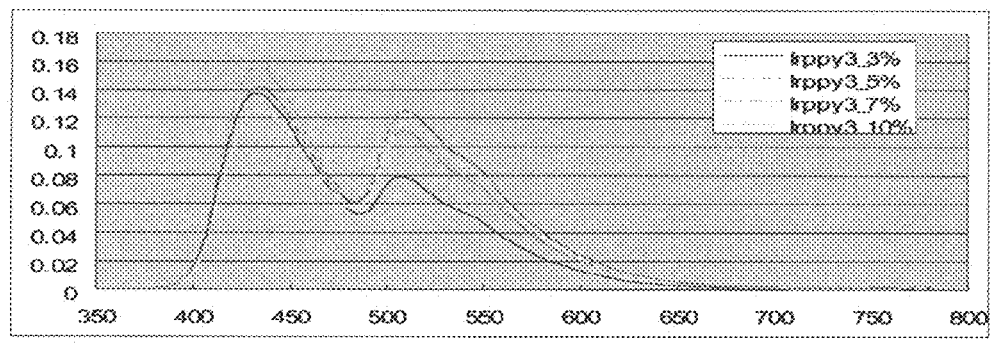
FIG. 27 is a graph showing variations in the luminescence intensity of an organic electroluminescent device (Example 12) employing a green phosphorescent dopant at various doping concentrations.

Organic electroluminescent devices were fabricated in the same manner as in Example 10 except that Ir(ppy)$_3$ was used as a dopant. See, FIG. 27.

Example 13: Fabrication of Organic Electroluminescent Device [K-2 (40 nm) BT (7 wt %)]

Figure 28:
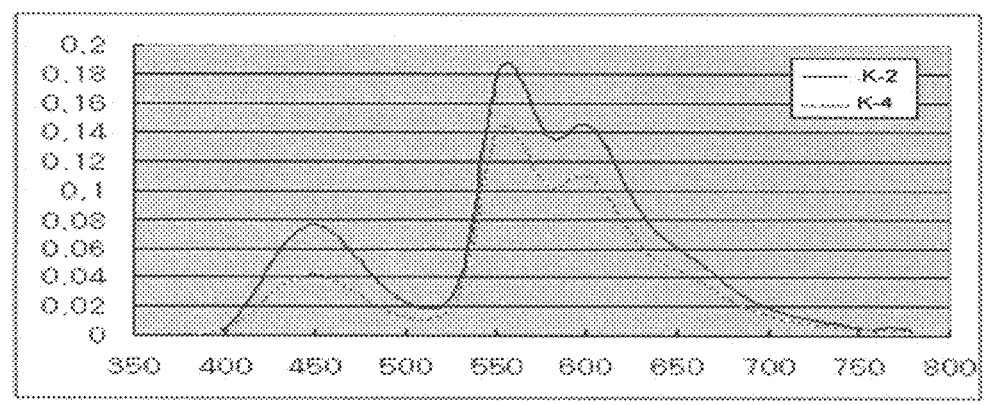
FIG. 28 is a graph showing variations in the luminescence intensity of organic electroluminescent devices fabricated in Examples 13 and 15.

An organic electroluminescent device was fabricated in the same manner as in Example 7 except that the material (K-2) of Formula 4 was used as a KL host material. See, FIG. 28.

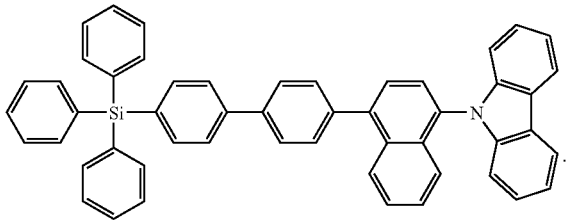

(4)

Example 14: Fabrication of Organic Electroluminescent Device [K-3 (40 nm) BT (7%)]

Figure 29:
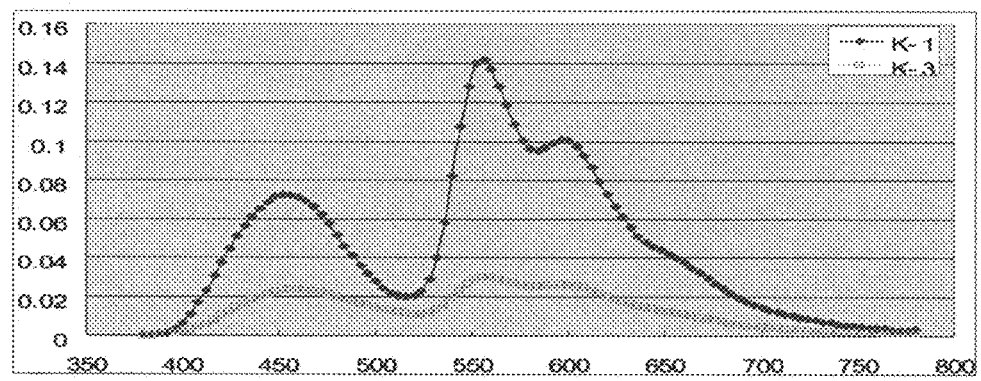
FIG. 29 is a graph showing variations in the luminescence intensity of an organic electroluminescent device fabricated in Example 14.

An organic electroluminescent device was fabricated in the same manner as in Example 7 except that the material (K-3) of Formula 5 was used as a KL host material. See, FIG. 29.

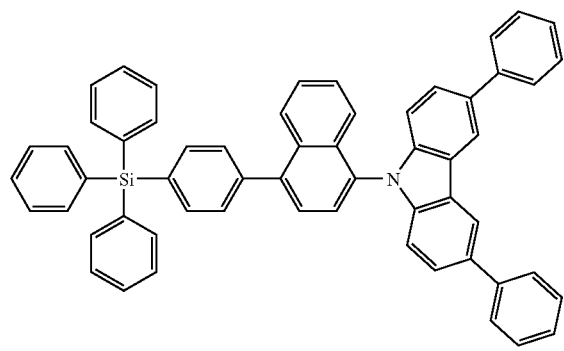

(5)

Example 15: Fabrication of Organic Electroluminescent Device [K-4 (40 nm) BT (7%)]

An organic electroluminescent device was fabricated in the same manner as in Example 7 except that the material (K-4) of Formula 7 was used as a KL host material. See, FIG. 28.

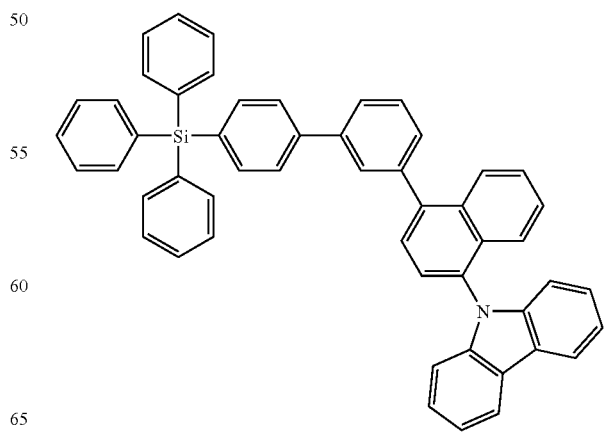

(6)

Comparative Example 1: Fabrication of Organic Electroluminescent Device [CBP (40 nm) BTP (7 wt %)]

Figure 30:
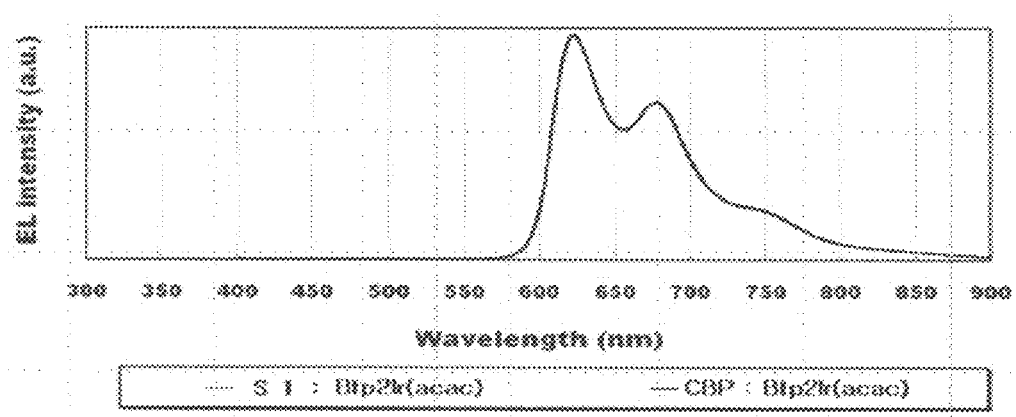
FIG. 30 is a graph showing variations in the luminescence intensity of devices (Comparative Examples 1 and 2) employing a host material having a structure similar to that of a KL host material.

An organic electroluminescent device was fabricated in the same manner as in Example 7 except that 4,4'-bis(carbazol-9-yl)-2,2'-biphenyl (CBP) was used as a host material and Btp$_2$Ir(acac)bis(2-(2'-benzo[4,5-α]thienyl)pyridinato-N, C3')iridium(acetylactonate) (BTP) was used as a dopant. See, FIG. 30.

Comparative Example 2: Fabrication of Organic Electroluminescent Device [S-1 (40 nm) BTP (7 wt %)]

An organic electroluminescent device was fabricated in the same manner as in Comparative Example 1 except that the material (S-1) of Formula 7, whose structure is similar to the KL host material but whose substituents fall outside the range defined in the KL host material, was used as a host material. See, FIG. 30.

(7)

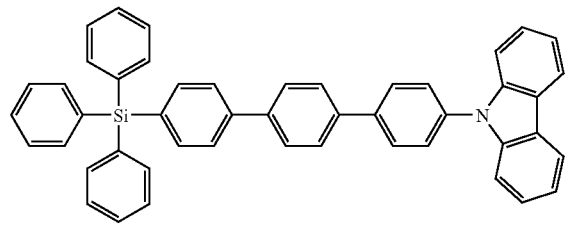

Comparative Examples 3 and 4: Fabrication of Organic Electroluminescent Devices [S-1 (40 nm) Ir(ppy)$_3$ (7 wt %)]

Figure 31:
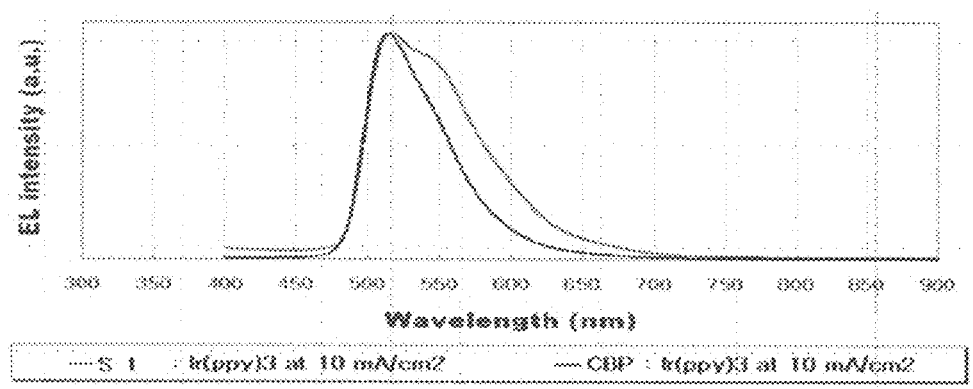
FIG. 31 is a graph showing variations in the luminescence intensity of devices (Comparative Examples 3 and 4) employing a host material having a structure similar to that of a KL host material.

Organic electroluminescent devices were fabricated in the same manner as in Comparative Examples 3 and 4 except that Ir(ppy)$_3$ was used as a dopant. See, FIG. 31.

Experimental Example 1: Evaluation of Devices

1) Operating Voltage

Variations in the current density of the organic electroluminescent devices fabricated in Examples 1-15 and Comparative Examples 1-4 were measured in response to changes in voltage. Currents flowing through the unit devices were measured using a current-voltage measurement unit (Keithley SMU 237) while increasing the current density from 2.5 mA/cm$^2$ to 100 mA/cm$^2$ with an increment of 2.5 mA.

2) Chromaticity Coordinates

The chromaticity coordinates of the organic electroluminescent devices were measured using a colorimeter (Photo Research PR-650) while increasing the current density from 2.5 mA/cm$^2$ to 100 mA/cm$^2$ with an increment of 2.5 mA.

3) Efficiency

The luminescence efficiency of the organic electroluminescent devices was calculated from the luminance and the current density values.

4) EL Max

EL max was defined as a wavelength corresponding to the maximum intensity in each of the spectra (FIGS. 7-31) of the organic electroluminescent devices taken using a luminance meter (Photo Research PR-650) while supplying power from a source unit (Keithley SMU 237) to the devices.

The results are shown in Tables 1-11. In FIGS. 7-31, the y-axis shows EL intensity (a.u.) and the x-axis shows wavelength (nm).

TABLE 1

Results of Example 1

| [Volt (V)] | [Curr. Dens] | [Cd/m2] | [Cd/A] | [lm/W] | [x] | [y] |
|---|---|---|---|---|---|---|
| 11.2 | 10 | 140 | 1.38 | 0.39 | 0.15 | 0.09 |
| 12.0 | 20 | 270 | 1.35 | 0.35 | 0.15 | 0.09 |
| 13.8 | 50 | 660 | 1.32 | 0.30 | 0.15 | 0.09 |
| 15.3 | 100 | 1150 | 1.15 | 0.24 | 0.15 | 0.09 |

TABLE 2

Results of Example 2

| [Volt (V)] | [Curr. Dens] | [Cd/m2] | [Cd/A] | [lm/W] | [x] | [y] |
|---|---|---|---|---|---|---|
| 10.54 | 10 | 766.8 | 7.649 | 2.279 | 0.394 | 0.388 |
| 11.83 | 20 | 1495 | 7.46 | 1.981 | 0.39 | 0.384 |
| 12.89 | 50 | 3396 | 6.787 | 1.654 | 0.38 | 0.373 |
| 13.91 | 100 | 5997 | 5.992 | 1.354 | 0.373 | 0.366 |

TABLE 3

Results of Example 3

| [Volt (V)] | [Curr. Dens] | [Cd/m2] | [Cd/A] | [lm/W] | [x] | [y] |
|---|---|---|---|---|---|---|
| 9.93 | 10 | 217.5 | 2.169 | 0.686 | 0.148 | 0.12 |
| 11.03 | 20 | 424 | 2.116 | 0.602 | 0.148 | 0.119 |
| 12.58 | 50 | 1009 | 2.017 | 0.504 | 0.149 | 0.117 |
| 13.2 | 100 | 1902 | 1.9 | 0.452 | 0.149 | 0.114 |

TABLE 4

Results of Example 4

| [Volt (V)] | [Curr. Dens] | [Cd/m2] | [Cd/A] | [lm/W] | [x] | [y] |
|---|---|---|---|---|---|---|
| 11.49 | 10 | 247.6 | 2.47 | 0.675 | 0.366 | 0.344 |
| 12.89 | 20 | 448.5 | 2.238 | 0.546 | 0.371 | 0.35 |
| 15.2 | 50 | 1008 | 2.015 | 0.417 | 0.366 | 0.348 |
| 16.07 | 100 | 1576 | 1.575 | 0.308 | 0.352 | 0.343 |

TABLE 5

Results of Example 5

| [Volt (V)] | [Curr. Dens] | [Cd/m2] | [Cd/A] | [lm/W] | [x] | [y] |
|---|---|---|---|---|---|---|
| 10.47 | 10 | 683.9 | 6.822 | 2.046 | 0.387 | 0.382 |
| 11.68 | 20 | 1369 | 6.832 | 1.837 | 0.385 | 0.381 |
| 13.38 | 50 | 3190 | 6.377 | 1.497 | 0.377 | 0.372 |
| 14.36 | 100 | 5636 | 5.632 | 1.232 | 0.371 | 0.366 |

TABLE 6

Results of Example 6

| [Volt (V)] | [Curr. Dens] | [Cd/m2] | [Cd/A] | [lm/W] | [x] | [y] |
|---|---|---|---|---|---|---|
| 8.28 | 9.44 | 428.3 | 4.537076 | 1.720582 | 0.18 | 0.255 |
| 9.44 | 19.44 | 859.8 | 4.42284 | 1.471156 | 0.186 | 0.254 |
| 11.01 | 49.44 | 2071 | 4.188916 | 1.194659 | 0.193 | 0.253 |
| 12.31 | 99.44 | 3869 | 3.890788 | 0.992451 | 0.199 | 0.252 |

TABLE 7

Results of Example 7

| [Volt (V)] | [Curr. Dens] | [Cd/m2] | [Cd/A] | [lm/W] | [x] | [y] |
|---|---|---|---|---|---|---|
| 7.73 | 10 | 1564 | 15.611 | 6.343 | 0.476 | 0.462 |
| 8.65 | 20 | 3110 | 15.561 | 5.649 | 0.469 | 0.453 |
| 9.76 | 50 | 6530 | 13.056 | 4.202 | 0.453 | 0.435 |
| 10.53 | 100 | 10230 | 10.225 | 3.051 | 0.438 | 0.417 |

TABLE 8

Results of Example 8 [KL-1 (40 nm)__BT (3, 5, 7 and 10 wt %)]

| Volt (V) | Current (mA) | J (mA/cm2) | J (A/m2) | Cd/A | lm/W | Cd/m2 | CIEx | CIEy | QE |
|---|---|---|---|---|---|---|---|---|---|
| 8.1551 | 0.4 | 10 | 100 | 14.71 | 5.664 | 1471 | 0.4648 | 0.451 | 5.93% |
| 9.358 | 0.8 | 20 | 200 | 14.79 | 4.963 | 2958 | 0.4623 | 0.448 | 5.99% |
| 10.846 | 2 | 50 | 500 | 13.40 | 3.881 | 6702 | 0.4534 | 0.437 | 5.51% |
| 12.114 | 4 | 100 | 1000 | 12.05 | 3.123 | 12050 | 0.4412 | 0.422 | 5.06% |
| 7.4226 | 0.4 | 10 | 100 | 22.18 | 9.383 | 2218 | 0.4909 | 0.479 | 8.66% |
| 8.4435 | 0.8 | 20 | 200 | 23.23 | 8.637 | 4645 | 0.4892 | 0.476 | 9.07% |
| 9.921 | 2 | 50 | 500 | 21.38 | 6.767 | 10690 | 0.4834 | 0.47 | 8.44% |
| 11.244 | 4 | 100 | 1000 | 18.83 | 5.258 | 18830 | 0.4753 | 0.46 | 7.53% |
| 7.0286 | 0.4 | 10 | 100 | 25.47 | 11.379 | 2547 | 0.4973 | 0.484 | 9.88% |
| 7.9499 | 0.8 | 20 | 200 | 26.35 | 10.408 | 5270 | 0.4961 | 0.483 | 10.24% |
| 9.331 | 2 | 50 | 500 | 24.20 | 8.144 | 12100 | 0.492 | 0.478 | 9.46% |
| 10.613 | 4 | 100 | 1000 | 21.32 | 6.308 | 21320 | 0.4861 | 0.471 | 8.41% |
| 6.8509 | 0.4 | 10 | 100 | 22.66 | 10.386 | 2266 | 0.5021 | 0.486 | 8.84% |
| 7.7909 | 0.8 | 20 | 200 | 24.63 | 9.927 | 4926 | 0.5014 | 0.485 | 9.63% |
| 9.18 | 2 | 50 | 500 | 23.86 | 8.161 | 11930 | 0.4985 | 0.482 | 9.35% |
| 10.455 | 4 | 100 | 1000 | 21.57 | 6.478 | 21570 | 0.494 | 0.477 | 8.52% |

TABLE 9

Results of Example 9 [KL-1 (40 nm)__Bzq (3, 5, 7 and 10 wt %)]

| Volt (V) | Current (mA) | J (mA/cm2) | J (A/m2) | Cd/A | lm/W | Cd/m2 | CIEx | CIEy | QE |
|---|---|---|---|---|---|---|---|---|---|
| 7.9079 | 0.4 | 10 | 100 | 18.05 | 7.167 | 1805 | 0.3996 | 0.512 | 5.98% |
| 8.8352 | 0.8 | 20 | 200 | 16.03 | 5.697 | 3206 | 0.3914 | 0.499 | 5.40% |
| 10.174 | 2 | 50 | 500 | 12.93 | 3.989 | 6463 | 0.3747 | 0.472 | 4.54% |
| 11.409 | 4 | 100 | 1000 | 10.54 | 2.901 | 10540 | 0.357 | 0.443 | 3.88% |
| 7.2808 | 0.4 | 10 | 100 | 23.00 | 9.919 | 2300 | 0.4106 | 0.526 | 7.46% |
| 8.2294 | 0.8 | 20 | 200 | 20.51 | 7.826 | 4102 | 0.4024 | 0.513 | 6.77% |
| 9.536 | 2 | 50 | 500 | 16.06 | 5.288 | 8030 | 0.3871 | 0.49 | 5.49% |
| 10.75 | 4 | 100 | 1000 | 12.90 | 3.768 | 12900 | 0.3703 | 0.463 | 4.59% |
| 6.8636 | 0.4 | 10 | 100 | 22.20 | 10.156 | 2220 | 0.424 | 0.522 | 7.33% |
| 7.7042 | 0.8 | 20 | 200 | 21.00 | 8.559 | 4200 | 0.4174 | 0.513 | 7.02% |
| 8.933 | 2 | 50 | 500 | 17.37 | 6.106 | 8686 | 0.4055 | 0.497 | 5.93% |
| 10.125 | 4 | 100 | 1000 | 14.76 | 4.577 | 147.60 | 0.3919 | 0.477 | 5.18% |
| 6.9866 | 0.4 | 10 | 100 | 18.45 | 8.292 | 1845 | 0.4288 | 0.52 | 6.14% |
| 7.8933 | 0.8 | 20 | 200 | 18.24 | 7.256 | 3648 | 0.4228 | 0.511 | 6.13% |
| 9.221 | 2 | 50 | 500 | 16.26 | 5.536 | 8129 | 0.411 | 0.496 | 5.57% |
| 10.442 | 4 | 100 | 1000 | 14.07 | 4.231 | 14070 | 0.3979 | 0.478 | 4.95% |

TABLE 10

Results of Example 10 [KL-1 (40 nm)__Tbpiq (3, 5, 7 and 10 wt %)]

| Volt (V) | Current (mA) | J (mA/cm2) | J (A/m2) | Cd/A | lm/W | Cd/m2 | CIEx | CIEy | QE |
|---|---|---|---|---|---|---|---|---|---|
| 7.2608 | 0.4 | 10 | 100 | 8.91 | 3.851 | 890.6 | 0.6493 | 0.307 | 11.60% |
| 8.2597 | 0.8 | 20 | 200 | 8.36 | 3.176 | 1671 | 0.6407 | 0.303 | 10.85% |
| 8.8586 | 1.2 | 30 | 300 | 7.76 | 2.751 | 2328 | 0.634 | 0.301 | 10.06% |
| 9.29 | 1.6 | 40 | 400 | 7.32 | 2.473 | 2927 | 0.6279 | 0.298 | 9.47% |
| 9.619 | 2 | 50 | 500 | 6.93 | 2.262 | 3464 | 0.6224 | 0.296 | 8.95% |
| 10.901 | 4 | 100 | 1000 | 5.74 | 1.655 | 5744 | 0.5983 | 0.285 | 7.40% |
| 7.3772 | 0.4 | 10 | 100 | 9.95 | 4.237 | 995.4 | 0.6545 | 0.308 | 13.30% |
| 8.3795 | 0.8 | 20 | 200 | 9.19 | 3.442 | 1837 | 0.6478 | 0.305 | 12.23% |
| 9.016 | 1.2 | 30 | 300 | 8.58 | 2.989 | 2575 | 0.6421 | 0.302 | 11.39% |
| 9.475 | 1.6 | 40 | 400 | 8.12 | 2.690 | 3247 | 0.6372 | 0.3 | 10.76% |
| 9.831 | 2 | 50 | 500 | 7.72 | 2.464 | 3858 | 0.6326 | 0.299 | 10.21% |
| 11.202 | 4 | 100 | 1000 | 6.42 | 1.801 | 6424 | 0.6124 | 0.29 | 8.45% |
| 7.1231 | 0.4 | 10 | 100 | 9.45 | 4.167 | 945.3 | .0.6606 | 0.309 | 13.04% |
| 8.0745 | 0.8 | 20 | 200 | 8.88 | 3.451 | 1775 | 0.6552 | 0.306 | 12.21% |
| 8.6858 | 1.2 | 30 | 300 | 8.42 | 3.043 | 2525 | 0.6509 | 0.305 | 11.55% |
| 9.139 | 1.6 | 40 | 400 | 8.06 | 2.768 | 3223 | 0.6471 | 0.303 | 11.03% |
| 9.502 | 2 | 50 | 500 | 7.75 | 2.561 | 3875 | 0.6436 | 0.302 | 10.58% |
| 10.853 | 4 | 100 | 1000 | 6.65 | 1.923 | 6648 | 0.6284 | 0.296 | 9.02% |
| 7.0171 | 0.4 | 10 | 100 | 8.25 | 3.693 | 825.2 | 0.6691 | 0.311 | 11.69% |
| 7.952 | 0.8 | 20 | 200 | 7.93 | 3.129 | 1585 | 0.6653 | 0.31 | 11.18% |
| 8.555 | 1.2 | 30 | 300 | 7.62 | 2.797 | 2286 | 0.6625 | 0.309 | 10.73% |
| 8.9853 | 1.6 | 40 | 400 | 7.29 | 2.548 | 2916 | 0.66 | 0.308 | 10.24% |
| 9.338 | 2 | 50 | 500 | 7.09 | 2.384 | 3545 | 0.6576 | 0.307 | 9.92% |
| 10.668 | 4 | 100 | 1000 | 6.26 | 1.843 | 6262 | 0.6472 | 0.303 | 8.71% |

TABLE 11

Results of Example 11 [KL-1_Bzq (6%)/Tbpiq (7%)]

|  | Volt (V) | Current (mA) | J (mA/cm2) | J (A/m2) | Cd/A | lm/W | Cd/m2 | CIEx | CIEy | QE |
|---|---|---|---|---|---|---|---|---|---|---|
| 35 × 35 | 9.358 | 0.4 | 10 | 100 | 24.71 | 8.291 | 2471 | 0.4677 | 0.51 | 9.97% |
|  | 10.661 | 0.8 | 20 | 200 | 22.27 | 6.559 | 4454 | 0.4643 | 0.51 | 8.94% |
|  | 11.449 | 1.2 | 30 | 300 | 20.62 | 5.656 | 6187 | 0.4616 | 0.509 | 8.23% |
|  | 12.032 | 1.6 | 40 | 400 | 19.56 | 5.105 | 7825 | 0.4593 | 0.509 | 7.78% |
|  | 12.443 | 2 | 50 | 500 | 18.49 | 4.665 | 9243 | 0.4574 | 0.509 | 7.34% |
|  | 14.115 | 4 | 100 | 1000 | 15.62 | 3.475 | 15620 | 0.4501 | 0.507 | 6.14% |
| 35 × 20 | 9.338 | 0.4 | 10 | 100 | 23.83 | 8.013 | 2383 | 0.4489 | 0.521 | 8.78% |
|  | 10.572 | 0.8 | 20 | 200 | 21.30 | 6.325 | 4259 | 0.4445 | 0.519 | 7.81% |
|  | 11.346 | 1.2 | 30 | 300 | 19.61 | 5.427 | 5883 | 0.4412 | 0.517 | 7.18% |
|  | 11.895 | 1.6 | 40 | 400 | 18.30 | 4.830 | 7319 | 0.4384 | 0.516 | 6.96% |
|  | 12.306 | 2 | 50 | 500 | 17.13 | 4.371 | 8566 | 0.4361 | 0.514 | 6.25% |
|  | 13.917 | 4 | 100 | 1000 | 14.00 | 3.159 | 14000 | 0.4272 | 0.507 | 5.12% |
| 35 × 25 | 9.118 | 0.4 | 10 | 100 | 18.44 | 6.350 | 1844 | 0.4466 | 0.5 | 7.34% |
|  | 10.352 | 0.8 | 20 | 200 | 16.79 | 5.093 | 3358 | 0.4402 | 0.496 | 6.65% |
|  | 11.12 | 1.2 | 30 | 300 | 15.59 | 4.401 | 4676 | 0.4354 | 0.493 | 6.17% |
|  | 11.655 | 1.6 | 40 | 400 | 14.64 | 3.944 | 5855 | 0.4314 | 0.49 | 5.79% |
|  | 12.08 | 2 | 50 | 500 | 13.86 | 3.602 | 6928 | 0.4279 | 0.487 | 5.48% |
|  | 13.663 | 4 | 100 | 1000 | 11.50 | 2.643 | 11500 | 0.415 | 0.475 | 4.57% |
| 35 × 20 | 8.4662 | 0.4 | 10 | 100 | 19.79 | 7.340 | 1979 | 0.4588 | 0.49 | 8.52% |
|  | 9.598 | 0.8 | 20 | 200 | 17.66 | 5.777 | 3532 | 0.4526 | 0.484 | 7.62% |
|  | 10.284 | 1.2 | 30 | 300 | 16.05 | 4.902 | 4816 | 0.448 | 0.48 | 6.94% |
|  | 10.77 | 1.6 | 40 | 400 | 15.03 | 4.381 | 6010 | 0.4442 | 0.477 | 6.50% |
|  | 11.154 | 2 | 50 | 500 | 14.01 | 3.944 | 7005 | 0.441 | 0.474 | 6.07% |
|  | 12.724 | 4 | 100 | 1000 | 12.03 | 2.969 | 12030 | 0.4269 | 0.461 | 5.25% |
| 30 × 35 | 7.9823 | 0.4 | 10 | 100 | 23.22 | 9.134 | 2322 | 0.435 | 0.507 | 8.54% |
|  | 9.043 | 0.8 | 20 | 200 | 20.97 | 7.281 | 4194 | 0.4287 | 0.5 | 7.75% |
|  | 9.687 | 1.2 | 30 | 300 | 19.25 | 6.241 | 5776 | 0.4243 | 0.496 | 7.14% |
|  | 10.181 | 1.6 | 40 | 400 | 18.23 | 5.622 | 7292 | 0.4205 | 0.492 | 6.78% |
|  | 10.558 | 2 | 50 | 500 | 17.33 | 5.155 | 8667 | 0.4172 | 0.489 | 6.46% |
|  | 11.942 | 4 | 100 | 1000 | 14.37 | 3.778 | 14370 | 0.4054 | 0.476 | 5.41% |
| 30 × 30 | 7.5724 | 0.4 | 10 | 100 | 22.35 | 9.268 | 2235 | 0.4365 | 0.501 | 8.37% |
|  | 8.5597 | 0.8 | 20 | 200 | 19.90 | 7.298 | 3979 | 0.4304 | 0.493 | 7.51% |
|  | 9.201 | 1.2 | 30 | 300 | 18.31 | 6.250 | 5494 | 0.4259 | 4.488 | 6.97% |
|  | 9.674 | 1.6 | 40 | 400 | 17.18 | 5.576 | 6872 | 0.4221 | 0.483 | 6.57% |
|  | 10.065 | 2 | 50 | 500 | 16.57 | 5.075 | 8133 | 0.4188 | 0.48 | 6.25% |
|  | 11.463 | 4 | 100 | 1000 | 13.53 | 3.706 | 13530 | 0.4062 | 0.465 | 5.27% |
| 30 × 25 | 7.6374 | 0.4 | 10 | 100 | 20.61 | 8.473 | 2061 | 0.4286 | 0.485 | 8.06% |
|  | 8.6576 | 0.8 | 20 | 200 | 18.26 | 6.623 | 3652 | 0.4199 | 0.473 | 7.25% |
|  | 9.29 | 1.2 | 30 | 300 | 16.76 | 5.665 | 5028 | 0.4135 | 0.465 | 6.72% |
|  | 9.756 | 1.6 | 40 | 400 | 15.69 | 5.050 | 6276 | 0.4084 | 0.458 | 6.35% |
|  | 10.112 | 2 | 50 | 500 | 14.77 | 4.587 | 7386 | 0.4042 | 0.453 | 6.03% |
|  | 11.456 | 4 | 100 | 1000 | 12.29 | 3.369 | 12290 | 0.3881 | 0.432 | 5.14% |
| 30 × 20 | 7.1486 | 0.4 | 10 | 100 | 19.47 | 8.552 | 1947 | 0.4344 | 0.477 | 8.02% |
|  | 8.0819 | 0.8 | 20 | 200 | 17.10 | 6.642 | 3419 | 0.4251 | 0.464 | 7.18% |
|  | 8.6604 | 1.2 | 30 | 300 | 15.55 | 5.638 | 4665 | 0.4185 | 0.454 | 6.62% |
|  | 9.084 | 1.6 | 40 | 400 | 14.44 | 4.990 | 5774 | 0.4132 | 0.447 | 6.21% |
|  | 9.406 | 2 | 50 | 500 | 13.53 | 4.517 | 6766 | 0.4087 | 0.441 | 5.88% |
|  | 10.674 | 4 | 100 | 1000 | 11.22 | 3.301 | 11220 | 0.391 | 0.418 | 5.03% |

Figure 9:
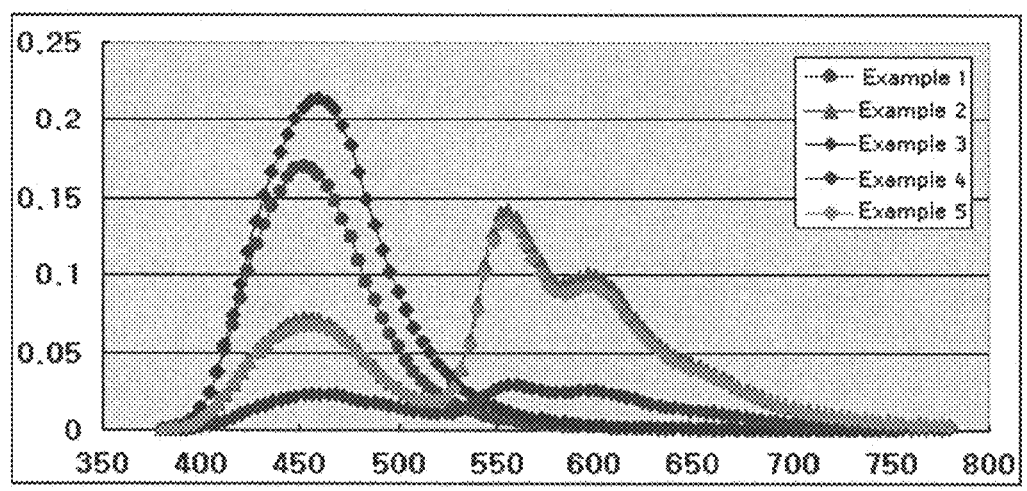
FIG. 9 shows electroluminescence (EL) spectra of an organic electroluminescent device (Example 1) employing a KL host material, an organic electroluminescent device (Example 3) employing a KL host material and a fluorescent dopant, and organic electroluminescent devices (Examples 2, 4 and 5), each of which employed a KL host material and a phosphorescent dopant.
Figure 10:
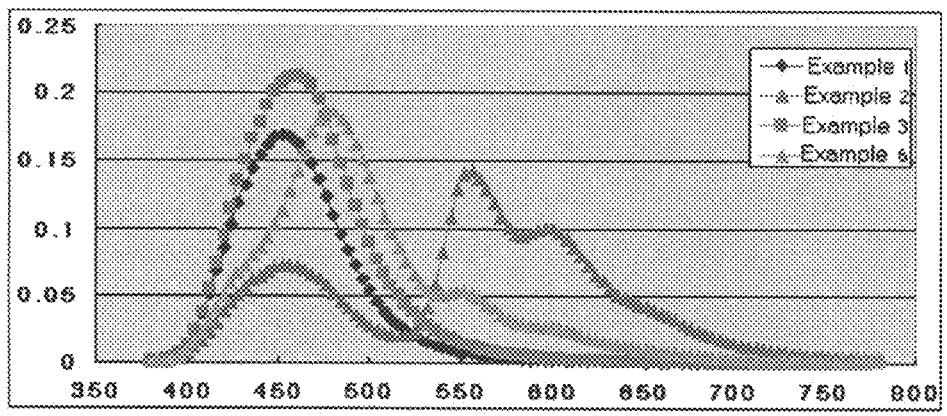
FIG. 10 shows EL spectra of an organic electroluminescent device employing a KL host material (Example 1), an organic electroluminescent device employing a KL host material and a fluorescent dopant (Example 3), an organic electroluminescent device employing a KL host material and a phosphorescent dopant (Example 2), and an organic electroluminescent device employing a KL host material, a fluorescent dopant and a phosphorescent dopant (Example 6)
Figure 11:
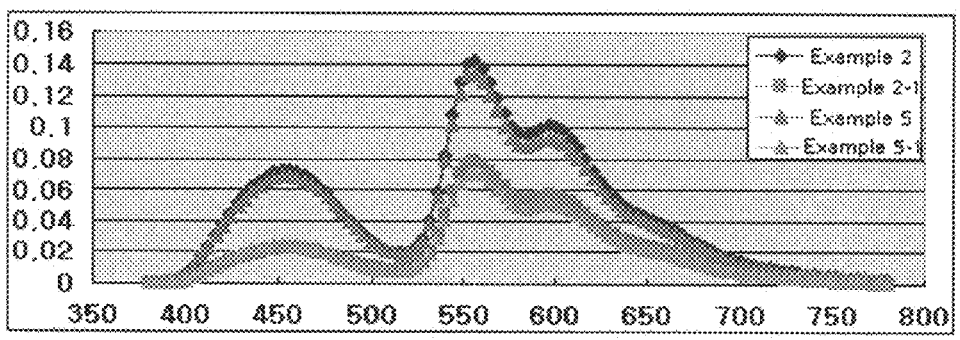
FIG. 11 shows variations in the EL spectra of organic electroluminescent devices (Examples 2 and 5) after half of the lifetimes of the devices.
Figure 12:
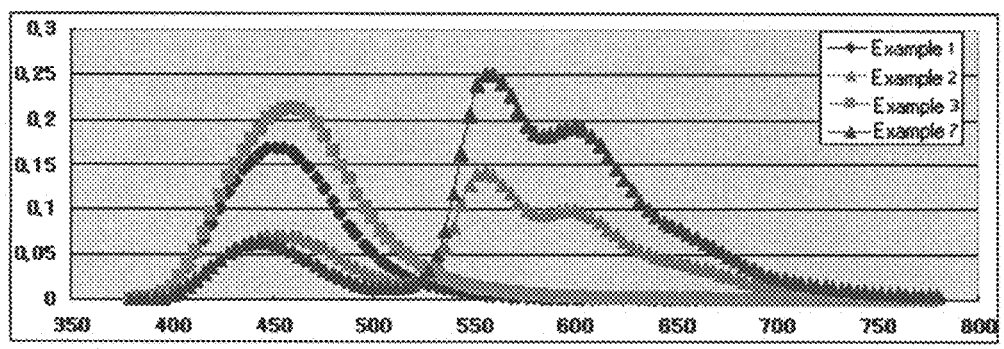
FIG. 12 shows EL spectra of organic electroluminescent devices (Examples 1, 2, 3 and 7) comprising no hole-blocking layer, demonstrating that the EL spectra are substantially the same as those of FIG. 10 and the efficiency of the devices is greatly improved.

As can be seen from the results in Tables 1-7 and FIGS. 7-13, each of the KL host materials emitted light of its own. In addition, when at least one dopant was added to the KL host material, light from the KL host material was combined with light from the dopant to emit high-luminance light (FIGS. 9 and 10). Because of simultaneous emission of light from the dopant and light from the KL host material, both fluorescence and phosphorescence emitted from the light-emitting layer could be mixed to emit light of various colors, e.g., white color. Further, the spectra of FIGS. 11 and 12 show that few changes in the color purity of each of the devices employing the KL host material were observed even after half of the lifetime of the device. A hole-blocking layer is generally formed when a phosphorescent material is used to form a light-emitting layer. In contrast, each of the devices employing the KL host material showed higher efficiency even in the absence of a hole-blocking layer. Based on these advantages, the KL host material can be employed to fabricate organic electroluminescent devices with high efficiency while reducing the number of processing steps.

The results in Tables 1, 2 and 7-11 and the corresponding FIGS. 13-19 show that the luminance and current efficiency of the organic electroluminescent device (Example 2) employing Compound 2 as a KL host material and a dopant were almost seven times higher than those of the organic electroluminescent device (Example 1) employing Compound 2 as a blue emitting material. Further, the luminance and maximum efficiency of the device (Example 7) comprising no hole-blocking layer almost doubled those of the device (Example 2) comprising a hole-blocking layer. These results reveal that the KL host material is very suitable as a host and effective in increasing the efficiency of the simpler structure comprising no hole-blocking layer.

According to the results (FIGS. 27-31) comparing the devices (Comparative Examples 1-4) employing CBP and S-1, which are well-known phosphorescent host materials, with the devices employing the KL host materials, the conventional host materials completely transferred their energy to the dopants and lost their energy to emit no light, while the devices employing the KL host materials emitted not only light in the long-wavelength region due to the energy transfer of the KL host materials to the dopants but also blue light from the KL host materials themselves.

In conclusion, the device employing the KL host material of the present invention exhibits high luminescence efficiency, which is attributed to light emission from a dopant due to the energy transfer of the KL host material to the dopant and light emission from the KL host material. Therefore, simultaneous emission of light from the KL host material and light from the dopant in a single light-emitting layer of the device facilitates polychromatic light emission (e.g., white light emission) and achieves high luminescence efficiency of the device.

Furthermore, the results in Table 11 and the corresponding FIGS. 19-26 demonstrate that the devices (Example 11) comprising two light-emitting layers containing different dopants deposited on the same KL host material showed higher luminance and more greatly increased current efficiency than the respective single light-emitting layers, indicating that the luminescence efficiency of the devices of Example 11 was much higher than that of the conventional devices. These results lead to the conclusion that the kind and concentration of the dopants and the thickness of the light-emitting layers can be varied to produce various colors from the devices, indicating high color reproducibility of the devices.

Industrial Applicability

As apparent from the above description, the KL host material of the present invention can be combined with at least one dopant to form a light-emitting layer of an organic electroluminescent device. Unlike conventional organic electroluminescent devices, the organic electroluminescent device of the present invention exhibits high luminescence efficiency due to simultaneous emission of light from the dopant and light from the KL host material. In addition, light emission from the KL host material and light emission from the dopant simultaneously occur in a single light-emitting layer, which makes the structure of the organic electroluminescent device relatively simple. Furthermore, phosphorescent and fluorescent dopants can be combined with the KL host material, resulting in high color reproducibility of the device. The single light-emitting layer facilitates the fabrication of the device. Moreover, the combined use of two or more different dopants (e.g., different fluorescent dopants, a fluorescent dopant/a phosphorescent dopant or different phosphorescent dopants) and the same KL host material for the formation of the light-emitting layer results in a markedly increased luminance and a relatively high luminescence efficiency of the device.

The invention claimed is:

1. A compound of Formula 1:

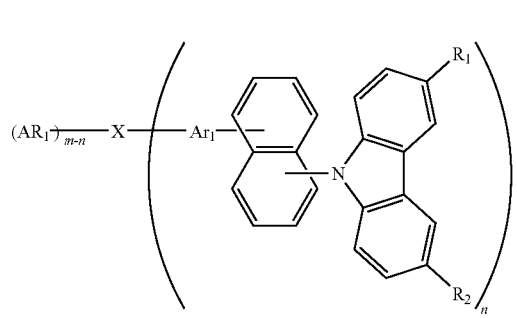

(1)

wherein each $Ar_1$ is selected from the group consisting of substituted or unsubstituted $C_6$-$C_{30}$ aromatic hydrocarbon groups which optionally contain at least one unsaturated aliphatic moiety, $C_2$-$C_{10}$ unsaturated aliphatic hydrocarbon groups, and substituted or unsubstituted $C_2$-$C_{24}$ unsaturated heterocyclic groups; $R_1$ and $R_2$ are each independently selected from the group consisting of hydrogen, $C_6$-$C_{24}$ aromatic hydrocarbon groups, and $C_6$-$C_{30}$ aromatic hydrocarbon groups containing at least one unsaturated aliphatic moiety; and X is selected from the group consisting of carbon, silicon, oxygen and sulfur, provided that when X is carbon or silicon, m is 4 and n is an integer from 1 to 4 and that when X is oxygen or sulfur, m is 2 and n is 1 or 2.

2. The compound according to claim 1, wherein each $Ar_1$ is selected from the following structures 2-1:

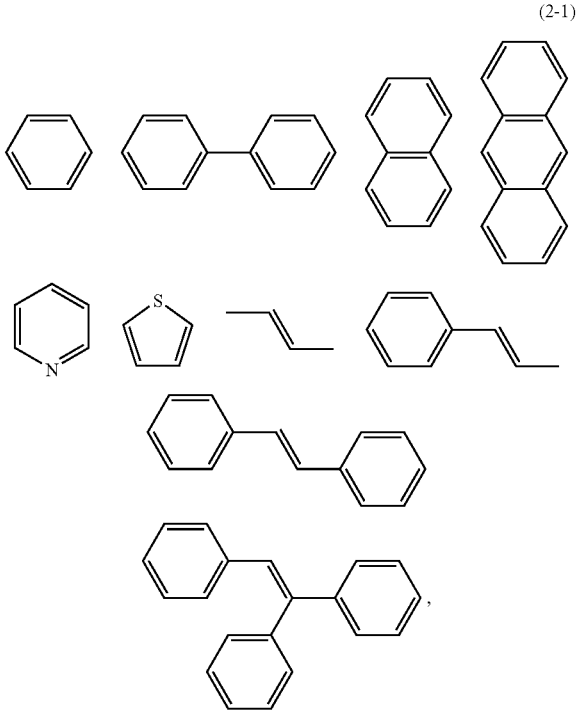

(2-1)

and $R_1$ and $R_2$ are each independently selected from the following structures 2-2:

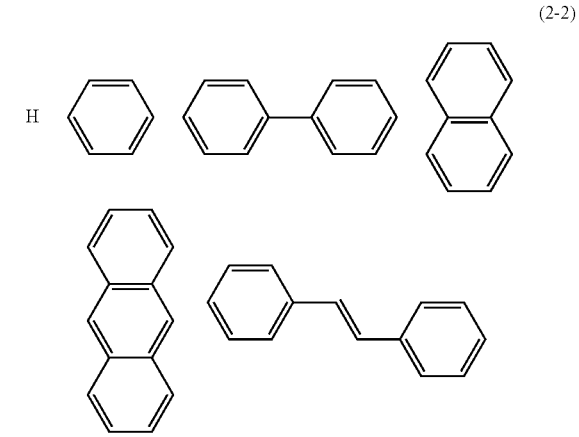

(2-2)

-continued

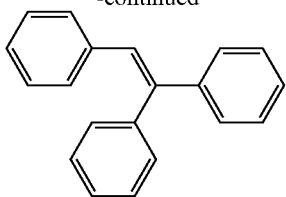

3. A KL host material for the formation of a light-emitting layer of an organic electroluminescent device wherein when the host material is combined with at least one dopant of fluorescent and phosphorescent dopants to form the light-emitting layer, energy of the host material is transferred to at least one dopant of the fluorescent and phosphorescent dopants to allow the dopant to emit light, and at the same time, the host material emits light of its own, and the host material material is the compound of Formula 1:

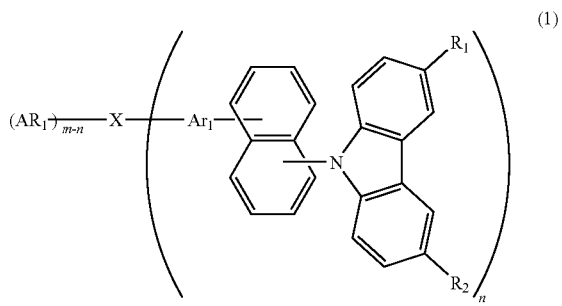

(1)

wherein each $Ar_1$ is selected from the group consisting of substituted or unsubstituted $C_6$-$C_{30}$ aromatic hydrocarbon groups which optionally contain at least one unsaturated aliphatic moiety, $C_2$-$C_{10}$ unsaturated aliphatic hydrocarbon groups, and substituted or unsubstituted $C_2$-$C_{24}$ unsaturated heterocyclic groups; $R_1$ and $R_2$ are each independently selected from the group consisting of hydrogen, $C_6$-$C_{24}$ aromatic hydrocarbon groups, and $C_6$-$C_{30}$ aromatic hydrocarbon groups containing at least one unsaturated aliphatic moiety; and X is selected from the group consisting of carbon, silicon, oxygen and sulfur, provided that when X is carbon or silicon, m is 4 and n is an integer from 1 to 4 and that when X is oxygen or sulfur, m is 2 and n is 1 or 2.

4. An organic electroluminescent device comprising an anode, a cathode and at least one light-emitting layer between the anode and the cathode wherein the light-emitting layer contains the KL host material according to claim 3.

5. The device according to claim 3, wherein the light-emitting layer further contains at least one dopant of phosphorescent and fluorescent dopants.

6. The device according to claim 4, wherein the KL host material emits light and the dopant emits light in a single layer.

7. The device according to claim 5, wherein the light-emitting layer simultaneously emits fluorescence and phosphorescence.

8. The device according to claim 4, wherein the light-emitting layer has a multilayer structure of two or more layers containing the KL host material and different dopants.

9. The device according to claim 7, wherein the light-emitting layer has a thickness of 1 to 60 nm.

10. The device according to claim 7, wherein the dopants are different phosphorescent dopants.

11. The device according to claim 4, wherein the dopant is present in an amount of 0.5 to 35 parts by weight, based on 100 parts by weight of the light-emitting layer.

12. The device according to claim 4, wherein light from the KL host material is mixed with light emitted from the dopant due to the energy transfer of the KL host material.

13. The device according to claim 11, wherein the mixed light is white light.

14. The device according to claim 4, wherein the KL host material emits blue light.

15. The device according to claim 4, wherein no hole-blocking layer is formed between the cathode and the light-emitting layer.

16. A display comprising the device according to claim 3.

17. A lighting system comprising the device according to claim 3.

* * * * *